US007629169B2

(12) United States Patent
Weiss et al.

(10) Patent No.: US 7,629,169 B2
(45) Date of Patent: Dec. 8, 2009

(54) METHODS FOR THE PRODUCTION OF PLATELET-DERIVED GROWTH FACTOR-RESPONSIVE NEURAL PRECURSOR CELLS

(75) Inventors: Samuel Weiss, Calgary (CA); Andrew Chojnacki, Calgary (CA)

(73) Assignee: Stem Cell Therapeutics Corp., Calgary, AB ( * ) Notice: Subject to any disclaimer, the term of this patent is extended or adjusted under 35 U.S.C. 154(b) by 0 days.

(21) Appl. No.: 11/292,326

(22) Filed: Dec. 1, 2005

(65) Prior Publication Data

US 2007/0009491 A1 Jan. 11, 2007

Related U.S. Application Data

(60) Provisional application No. 60/632,751, filed on Dec. 1, 2004, provisional application No. 60/738,735, filed on Nov. 21, 2005.

(51) Int. Cl.
*C12N 5/00* (2006.01)
*A01N 63/00* (2006.01)

(52) U.S. Cl. .................. 435/368; 435/377; 435/7.1; 424/93.7

(58) Field of Classification Search .................. None
See application file for complete search history.

(56) References Cited

U.S. PATENT DOCUMENTS

| 5,750,376 | A | 5/1998 | Weiss et al. |
|---|---|---|---|
| 5,753,506 | A | 5/1998 | Johe |
| 5,851,832 | A | 12/1998 | Weiss et al. |
| 5,980,885 | A | 11/1999 | Weiss et al. |
| 6,040,180 | A * | 3/2000 | Johe ............................ 435/377 |
| 6,251,669 | B1 * | 6/2001 | Luskin ........................ 435/375 |
| 6,887,706 | B2 * | 5/2005 | Zhang et al. ................ 435/377 |
| 2002/0098584 | A1 * | 7/2002 | Palmer et al. ............... 435/366 |
| 2002/0197238 | A1 | 12/2002 | Weiss et al. |
| 2003/0203844 | A1 | 10/2003 | Delfani et al. |

FOREIGN PATENT DOCUMENTS

| WO | WO/99 11758 | 3/1999 |
|---|---|---|
| WO | WO 01/88104 A2 | 11/2001 |
| WO | WO 02/088330 A2 | 11/2002 |

OTHER PUBLICATIONS

Bogler et al., "Cooperation Between Two Growth Factors Promotes Extended Self-Renewal and Inhibits Differentiation of Oligodendrocyte-Type-2 Astocyte 0-2A Progenitor Cells," Proc. of the Nat. Acad. Sci. USA, 87(16):6368-6372 (1990).
McKinnon et al., "FGF Modulates the PDGF-Driven Pathway of Oligodendrocyte Development," Neuron, 5(5):603-614 (1990).
Nishiyama et al., "Co-localization of NG2 proteoglycan and PDGF alpha-receptor on 02A progenitor cells in the developing rat brain," J. Neurosci. Res., 43(3):299-314 (1996).
Tang et al., "Long-term Culture of Purified Postnatal Oligodendrocyte Precursor Cells: Evidence for an Intrinsic Maturation Program That Plays Out Over Months," J. Cell Bio., 148(5):971-984 (2000).
Bogler et al., "Cooperation Between Two Growth Factors Promotes Extended Self-Renewal and Inhibits Differentation of Oligodendrocyte-Type-2 Astocyte 0-2A Progenitor Cells," Proc. Of the Nat. Acad. Sci. USA, 87(16):6368-6372 (1990).
Chojnacki et al, "Distinctions between embryonic and adult human PDGF-responsive neural precursors," The Canadian endMS Research Conference, Calgary, CA, Dec. 10-13, 2007.
Cua et al., "Matrix metalloproteinases degrade chondroitin sulfate proteoglycans and promote neurite outgrowth," The Canadian endMS Research Conference, Calgary, CA, Dec. 10-13, 2007.
McKinnon et al., "FGF Modulates the PDGF-Driven Pathway of Oligodendrocyte Development," Neuron, 5(5):603-614 (1990).
Nishiyama et al., "Co-localization of NG2 proteoglycan and PDGF alpha-receptor on 02A progenitor cells in the developing rat brain," J. Neurosco. Res., 43(3):299-314 (1996).
Tang et al., "Long-term Culture of Purified Postnatal Oligodendrocyte Precursor Cells: Evidence for an Intrinsic Maturation Program That Plays Out Over Months," J. Cell Bio., 148(5):971-984 (2000).
Ek, B., et al., Stimulation of Tyrosine-Specific Phosphorylation by Platelet-Derived Growth Factor, Nature 295:419-420 (1982).
Forsberg-Nilsson, K., et al., Platelet-Derived Growth Factor Induces Chemotaxis of Neuroepithelial Stem Cells, J. of Neuroscience Res., 53:521-530(1998).
Kondo, T., et al., Oligodendrocyte Precursor Cells Reprogrammed to Become Multipotential CNS Stem Cells, Science 289:1754-1757 (2000).
Nishimura, J., et al., Platelet-Derived Growth Factor Stimulates Tyrosine-Specific Protein Kinase Activity in Swiss Mouse 3T3 Cell Membranes, Proc. Natl. Acad. Sci USA, 79:4303-4307 (1982).
Chojnacki, A.K. and Weiss, S. "Platelet derived growth factor (PDGF)-derived neurospheres from the embryonic basal forebrain define a novel class of progenitor cells", Society for Neuroscience Abstracts 2001, vol. 27, No. 1, p. 348. (Abstract) BIOSIS [online] [retrieved on Mar. 09, 2003]. Retrieved from: STN International, Columbus, Ohio, USA. Accession No. 2001-486863.
Chojnacki, A. and Weiss, S. "Isolation of a Novel Platelet-Derived Growth Factor-Responsive Precusor from the Embryonic Ventral Forebrain", J Neurosci., Dec. 2004, No. 48, p. 10888-10899.
Database Biosis Online, "Platelet derived growth factor (PDGF)—derived neurospheres from the embryonic basal forebrain define a novel class of progenitor cells". Biosciences Information Service, database accession No. PREV200100486863 XP002215674 abstract & Society for Neuroscience Abstracts 2001, vol. 27, No. 1, p. 348.

(Continued)

*Primary Examiner*—Olga N Chernyshev
*Assistant Examiner*—Stacey MacFarlane
(74) *Attorney, Agent, or Firm*—Fish & Richardson P.C.

(57) ABSTRACT

This invention provides platelet-derived growth factor-responsive neural precursor (PRP) cells and methods of producing such cells in vivo or in vitro. These cells can further be used to generate neurons, oligodendrocytes and/or astrocytes.

18 Claims, 15 Drawing Sheets

OTHER PUBLICATIONS

Dirks, R. And Bloemers, H. "Signals controlling the expression of PDGF", Mol. Biology Reports 1996, vol. 22, No. 1-24.

Erlandsson, A. et al. "Immature Neurons From CNS Stem Cells Proliferate in Response to Platelet-Derived Growth Factor", J Neurosci., May 15, 2001, vol. 21, No. 10, p. 3483-3491.

Hannink, M. And Donoghue, D.J. "Structure and function of platelet-derived growth factor (PDGF) and related proteins", Biochim Biophys Acta. 1989, vol. 989, No. 1, p. 1-10.

Johe, K.K. et al. "Single factors direct the differentiation of stem cells from the fetal and adult central nervous system", Development 1996, vol. 10, p. 3129-3140.

Marmur, R. et al. "Isolation and development characterization of cerebral cortical multipotent progenitors", Developmental Biology 1998, vol. 204, No. 2, p. 577-591.

Reynolds, B.A. et al. "A Multipotent EGF-Responsive Striatal Embryonic Progenitor Cell Produces Neurons and Astrocytes", J of Neuro., Nov. 1992, vol. 12, No. 10, p. 4565-4574.

Rogister, B. et al. "From neural stem cells to myelinating oilgodendrocytes", Molecular and Cellular Neuroscience 1999, vol. 14, Nos. 4-5, p. 287-300.

Mohapel P., et al. "Platelet-derived growth factor (PDGF-BB) and brain-derived neurotrophic factor (BDNF) induce striatal neurogenesis in adult rats with 6-hydroxydopamine lesions." Neurosci. 132 (2005) 767-776.

Valenzuela, C.F. et al. "Roles of platelet-derived growth factor in the developing and mature nervous systems." Brain Res. Rev. 24 (1997) 77-89.

Chojnacki et al, "Distinctions between fetal and adult human platelet-derived growth factor-responsive neural precursors," Annals of Neurology 64(2):127-42 (2008).

* cited by examiner

FIGURE 6
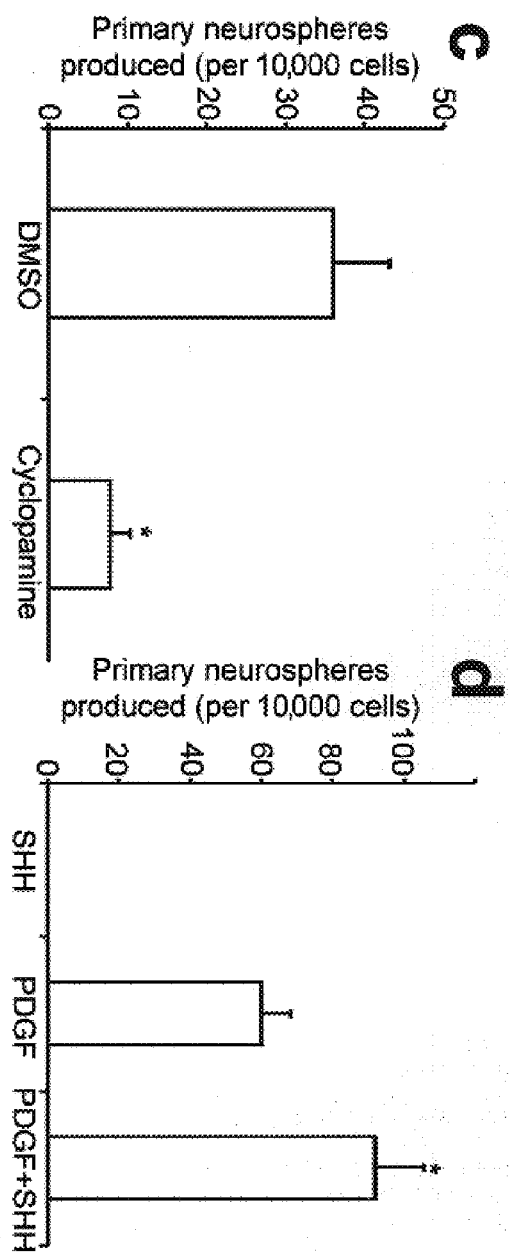
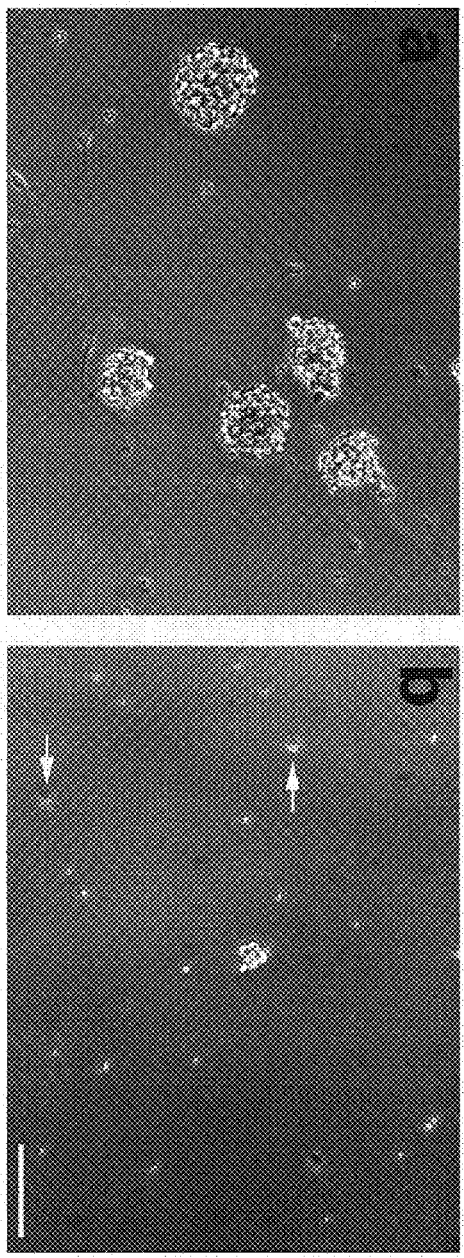

PRPs co-express PDGFRα and TrkC in the E14 ventral forebrain

PRPs do not co-express PDGFRα and TrkB in the E14 ventral forebrain

METHODS FOR THE PRODUCTION OF PLATELET-DERIVED GROWTH FACTOR-RESPONSIVE NEURAL PRECURSOR CELLS

RELATED APPLICATIONS

This application claims priority to application Ser. No. 60/632,751, filed Dec. 1, 2004, and application Ser. No. 60/738,735, filed Nov. 21, 2005, each of which are expressly incorporated by reference.

INTRODUCTION

Although there is general agreement about the factors involved in the development of oligodendrocyte progenitors (OLPs) throughout the central nervous system, their precise phenotype potential is highly contentious (Liu et al., *Trends Neurosci* 26:410 (2003); Noble et al., *Dev. Bio* 265:33 (2004); Rowitch, *Nat Rev Neurosci* 5:409 (2004)). Findings in the spinal cord, which show that similar levels of sonic hedgehog (SHH) signaling can induce motor neuron and oligodendrocyte cell fates (Pringle et al., *Dev Biol* 177:30 (1996); Orentas et al., *Development* 126:2419 (1999)) and that the basic helix-loop-helix transcriptional repressor Olig2 is required for the generation of both cell types (Lu et al., *Cell* 109:75 (2002)), are consistent with the idea that oligodendrocytes and motor neurons are generated by a common progenitor. In the brain, crosses of Olig1-CRE and Rosa-lox-β-Gal mice have revealed mutually exclusive expression of β-Gal and the astrocyte antigen S100β, while neurons and oligodendrocytes were labeled with β-Gal (Lu et al., *Cell* 109:75 (2002)) suggesting the latter were generated by a common precursor. However, the broad expression of OLIG1/2 in the embryonic forebrain compared to platelet-derived growth factor receptor-α (PDGFRα) (Tekki-Kessaris et al., *Development* 128: 2545 (2001)), an early OLP antigen, makes it difficult to determine whether neurons are generated by embryonic OLPs or non-related OLIG-expressing progenitors. Further support for a forebrain neuron/oligodendrocyte progenitor comes from observations that the tangential migration of both γ-aminobutyric acid (GABA)ergic interneurons and oligodendrocytes is disrupted in Dlx1/2 null mice (Yung et al., *Proc Natl Acad Sci USA* 99:16273 (2002)). However, the fact that taulacZ-positive astrocytes appear in mice that express taulacZ under the Dlx2 promoter (Marshall et al., *J Neurosci* 22:9821 (2002)) suggests that DLX-expressing cells may be either be multipotent or that DLX-expressing progenitors are a heterogeneous population.

In contrast to the studies reported above, crosses of Olig1-CRE and Rosa-lox-β-Gal mice have also shown that some OLIG1-expressing cells in the spinal cord eventually become astrocytes (Liu et al., *Glia* 45:67 (2004)), thereby providing in vivo evidence for an oligodendrocyte/astrocyte progenitor. Furthermore, the in vitro isolation of glial-restricted precursors (GRPs) from the spinal cord (Rao et al., *Dev Biol* 188:48 (1997); Rao et al., *Proc Natl Acad Sci USA* 95:3996 (1998)), and their transplantation and differentiation into astrocytes and oligodendrocytes (Rao et al., *Dev Biol* 188:48 (1997); Rao et al., *Proc Natl Acad Sci USA* 95:3996 (1998); Herrera et al., *Exp Neurol* 171:11 (2001)), supports such a lineage model. However, the fact that GRPs can be isolated from dorsal as well as ventral embryonic spinal cords contrasts with studies demonstrating the ventral restriction of OLPs (Warf et al., *J Neurosci* 11:2477 (1991); Pringle et al., *Development* 117:525 (1993); Ono et al., *Development* 121:1743 (1995); Lu et al., *Cell* 109:75 (2002); Zhou et al., *Cell* 109:61 (2002)). This may be reconciled by the findings of Gabay et al., *Neuron* 40:485 (2003), who found that the deregulation of dorsoventral patterning in vitro, due in part to aberrant SHH production induced by FGF signaling, may be responsible for the generation of oligodendrocytes by dorsally-derived GRPs. Nevertheless, a variety of studies in the brain, including in vivo retroviral-mediated lineage studies of the rat postnatal cerebral cortex (Levison et al., *Development* 119:611 (1993); Levison et al., *Neuron* 10:201 (1993)) as well as in vitro characterization of cortical OLPs (Mabie et al., *J Neurosci* 17:4112 (1997)) and optic nerve O-2A progenitors (Temple et al., *Nature* 313:223 (1985)), which never generate neurons, unless they are reprogrammed to become NSCs by their differentiation into astrocytes and subsequent expansion in FGF2 (Kondo et al., *Science* 289:1754 (2000)), support the contention that astrocytes and oligodendrocytes are generated by a common progenitor. However, retroviral tracing of the prenatal rat cortex revealed that glial clones were either oligodendroglial or astroglial (Parnavelas, *Exp Neurol* 156: 418 (1999)), although the same study also found mixed oligodendrocyte and astrocyte clones when injections of retrovirus were made into the postnatal SVZ. Interestingly, progenitors that express NG2, a chondroitin proteoglycan previously shown to co-localize to O-2A progenitors in vivo (Nishiyama et al., *J Neurosci Res* 43:299 (1996)), have been found to generate neurons in the postnatal hippocampus (Belachew et al., *J Cell Biol* 161:169 (2003)). However, these progenitors express the EGF receptor, have been identified as transit-amplifying type C-like multipotent cells (Aguirre et al., *J Cell Biol* 165:575 (2004)), and therefore whether they represent the differentiation properties of an OLP population is questionable. Thus, the cell types OLPs produce in the developing embryonic forebrain remains unclear.

SUMMARY

PDGF-responsive neural precursor (PRP) generated clonal cell expansions can be obtained from the medial ganglionic eminence (MGE), and PRP progeny can differentiate into parvalbumin-positive interneurons, oligodendrocytes, and astrocytes. Thyroid hormone (e.g., T3) and bone morphogenetic protein-2 (BMP-2) promote a mutually exclusive differentiation of oligodendrocytes and neurons, respectively, while ciliary neurotrophic factor (CNTF) acts with BMP-2 to suppress OLIG-2 expression and promote astroglial differentiation from PRP cells. PRPs clonally proliferate or undergo self-renewal in the presence of fibroblast growth factor-2 (FGF-2) with PDGF, which is dependent upon sonic hedgehog signaling (SHH). Evidence that forebrain oligodendrocytes and parvalbumin-positive interneurons are generated by a common precursor cell (PRP), and the signals regulating the multiple differentiation routes of PRP precursor cell progeny, is disclosed herein.

Isolated and purified mammalian platelet derived growth factor (PDGF)-responsive neural precursor (PRP) cells are provided, optionally expressing PDGF receptor alpha. In one embodiment, a cell, when contacted with one or more of thyroid hormone, bone morphogenetic protein-2 (BMP-2), ciliary neurotrophic factor (CNTF) or triiodothyronine (T3), gives rise to a differentiated neural cell that expresses detectable amounts of one or more protein markers selected from: GABA, parvalbumin, beta-II tubulin, calbindin D, calretinin, O4, neurofilament M (NFM), myelin basic protein (MBP), TOA-64/TUC-2 and GFAP. In another embodiment, a cell, when contacted with one or more of thyroid hormone, BMP-2, CNTF or T3, gives rise to a differentiated neuron, oligodendrocyte, astrocyte or mixture thereof.

Isolated and purified mammalian platelet derived growth factor (PDGF)-responsive neural precursor (PRP) cells are provided, optionally expressing PDGF receptor alpha, in which cells exhibit greater or less clonal proliferation when contacted with a factor or stimuli, or subjected to a condition, in vitro or in vivo. In various embodiments, a cell exhibits greater clonal proliferation when contacted with a PDGF receptor (PDGFR) agonist and an fibroblast growth factor (FGF) receptor agonist, then when contacted with either PDGF alone or epidermal growth factor (EGF) alone; a cell exhibits greater clonal proliferation when contacted with PDGF and brain derived neurotrophic factor (BDNF), then when contacted with either PDGF alone or EGF alone; or a cell exhibits greater clonal proliferation when contacted with PDGF and NT-3, then when contacted with either PDGF alone or EGF alone. In various aspects, clonal proliferation is induced or increased by stimulating sonic hedgehog signaling (SHH), or clonal proliferation is reduced or prevented by inhibition of sonic hedgehog signaling (SHH). In various additional embodiments, a cell exhibits less clonal proliferation under conditions of contact with PDGF than clonal proliferation of neural stem cell (NSC) under conditions of contact of NSC with EGF, a cell does not proliferate when contacted with EGF alone or FGF2 alone, or a cell proliferates when contacted with a PDGF receptor agonist and an FGF receptor agonist. In a further embodiment, a cell exhibits increased clonal proliferation when contacted with a PDGF receptor agonist and an FGF receptor agonist, as compared to clonal proliferation when contacted with PDGF alone, EGF alone or FGF2 alone.

Cells developmentally intermediate in the lineage with respect to PRP cells are and progeny thereof are also provided. In one embodiment, an intermediate cell is intermediate with respect to an undifferentiated cell and a neuron or oligodendrocyte. In another embodiment, an intermediate cell is designated an N/O cell and gives rise to a differentiated neuron or oligodendrocyte, but not an astrocyte, when contacted with one or more of BMP-2 or T3.

Isolated and purified populations of mammalian platelet derived growth factor (PDGF)-responsive neural precursor (PRP) cells, optionally expressing PDGF receptor alpha are provided, including progeny thereof. In one embodiment, at least a portion of the cell population gives rise to a differentiated neuron when contacted with BMP-2 and into an oligodendrocyte when contacted with triiodothyronine (T3). In another embodiment, at least a portion of the cell population gives rise to a differentiated astrocyte when contacted with BMP-2 and CNTF. In a further embodiment, at least a portion of the cell population gives rise to a differentiated astrocyte when contacted with T3 followed by contact with BMP-2 and CNTF. In an additional embodiment, the cells do not give rise to substantial numbers or detectable differentiated astrocytes, by contact with BMP-2 alone or CNTF alone.

Isolated and purified mammalian cell culture comprising undifferentiated and differentiated neural cells, optionally expressing PDGF receptor alpha, are further provided, including progeny thereof. In one embodiment, a cell culture includes about ⅓ of the total number of cells comprise differentiated beta-III-tubulin expressing neurons, and differentiated astrocytes are fewer in number or absent; or about ⅓ of the total number of cells comprise differentiated beta-III-tubulin expressing neurons and about ⅓ of the total number of cells in the culture comprise differentiated oligodendrocytes, and differentiated astrocytes are fewer in number or absent; or differentiated astrocytes are present in the cell culture, and ⅓ or less of the total number of cells in the culture comprise differentiated neurons; or about ⅔ of the total number of cells in the culture comprise differentiated astrocytes, and ⅓ or less of the total number of cells in the culture comprise differentiated neurons. In another embodiment, a cell culture includes neurons, and optionally at least 50%, 60%, 70%, 80% or more of the neurons express detectable amounts of parvalbumin or GABA.

Isolated and purified mammalian PRP cells, optionally expressing PDGF receptor alpha substantially free of connective tissue, are additionally provided, including progeny thereof. Isolated and purified PRP cells, optionally expressing PDGF receptor alpha dissociated from other cells or tissue, are additionally provided, including progeny thereof. In one aspect, PRP cell or progeny thereof have been contacted with a PDGFR agonist. In another aspect, PRP cell or progeny thereof are a culture of cells substantially free of differentiated neural cells.

Isolated and purified mammalian PRP cells, optionally expressing PDGF receptor alpha substantially including progeny thereof, include cells distinct from EGF-responsive neural stem cell (NSC). In one embodiment, a cell is more motile as compared to a progeny of EGF-responsive neural stem cell (NSC).

Mammalian PRP cells and progeny thereof can be obtained or derived from a nerve tissue or organ. In one embodiment, a cell includes or is derived from a primary brain cell isolate. In another embodiment, a cell includes or is derived from ganglionic eminence (e.g., medial ganglionic eminence, MGE).

Isolated and purified populations of mammalian platelet derived growth factor (PDGF)-responsive neural precursor (PRP) cells, optionally expressing PDGF receptor alpha are provided, including progeny thereof and cell populations, that have been contacted with a factor or stimuli, or subjected to or exposed to a condition, in vitro or in vivo. In one embodiment, a cell is or has been contacted with one or more of: PDGF, BDNF, NT-3, thyroid hormone, BMP-2, CNTF, EGF and T3.

Mammalian PRP cells and progeny thereof include human, primate, murine, rattus, bovine, porcine, equine, avian, cavia, lagomorph, canine or feline cells. Mammalian PDGF-responsive neural precursor (PRP) cells include cells obtained or derived from mammals; from an embryo, fetus, juvenile or adult.

Mammalian PRP cells and progeny thereof transformed with a nucleic acid are further provided. In one embodiment, a nucleic acid encodes a protein. In various aspects, a protein is a neurotransmitter, neurotransmitter receptor, growth factor, growth factor receptor, neurotransmitter-synthesizing enzyme, neurotransmitter receptor-synthesizing enzyme, growth factor-synthesizing enzyme, growth factor receptor-synthesizing enzyme, or a neuropeptide. In particular aspects, a protein is selected from brain-derived neurotrophic factor, neurotrophin, CNTF, amphiregulin, basic FGF, acidic FGF, EGF, transforming growth factor-alpha, transforming growth factor-beta, PDGF, insulin-like growth factor and interleukin. In additional particular aspects, a protein is selected from a low affinity nerve growth factor receptor, CNTF receptor, neurotrophin receptor, EGF receptor, FGF receptor and amphiregulin receptor. In further particular aspects, a protein is selected from a substance-P, neuropeptide-Y, enkephalin, vasopressin, vasoactive intestinal peptide, cholecystokinin, glucagon, bombesin, somatostatin, tachykinin, endorphin and calcitonin gene-related peptide. In still further particular aspects, a protein is selected from a tyrosine hydroxylase, tryptophan hydroxylase, phenylethanolamine N-methyltransferase, histidine decarboxylase, glutamic acid decarboxylase, choline acetyltransferase, dopa decarboxylase, dopamine beta hydroxylase and amino acid decarboxylase.

Cell cultures including PRP cell that express PDGF receptor alpha, including progeny thereof and cell populations, that have been contacted with a factor or stimuli, or subjected to or exposed to a condition, in vitro or in vivo, are additionally provided. In one embodiment, a cell culture has been contacted with a thyroid hormone, BMP-2, CNTF or T3, which gives rise to a differentiated neural cell that expresses detectable amounts of one or more protein markers selected from: GABA, parvalbumin, beta-II tubulin, calbindin D, calretinin, O4, neurofilament M (NFM), myelin basic protein (MBP), TOA-64/TUC-2 and GFAP. In another embodiment, a cell culture has been contacted with one or more of thyroid hormone, BMP-2, CNTF or T3, which gives rise to a differentiated neural cell that expresses detectable amounts of one or more protein markers selected from: GABA, parvalbumin, beta-II tubulin, calbindin D, calretinin, O4, neurofilament M (NFM), myelin basic protein (MBP), TOA-64/TUC-2 and GFAP.

Cell cultures including populations of cells enriched for mammalian PDGF-responsive neural precursor (PRP) cells that optionally express PDGF receptor alpha are moreover provided. In one embodiment, at least a portion of the enriched cells, when contacted with one or more of thyroid hormone, BMP-2, CNTF or T3, gives rise to a differentiated neural cell that expresses detectable amounts of one or more protein markers selected from: GABA, parvalbumin, beta-II tubulin, calbindin D, calretinin, O4, neurofilament M (NFM), myelin basic protein (MBP), TOA-64/TUC-2 and GFAP. In another embodiment, at least a portion of the enriched cells, when contacted with one or more of thyroid hormone, BMP-2, CNTF or T3, gives rise to a differentiated neuron, oligodendrocyte, astrocyte or mixture thereof.

Progeny of PDGF-responsive neural precursor (PRP) cells are provided. Progeny include clonally expanded cells, progenitor cells, and differentiated cells. Progeny include first, second, third, fourth, fifth, sixth seventh or any subsequent generation progeny cell or cells.

Pharmaceutical compositions including mammalian PDGF-responsive neural precursor (PRP) cells, as well as clonally expanded, progenitor or differentiated progeny cells thereof, and a pharmaceutically acceptable carrier or excipient, are provided. Kits including mammalian PDGF-responsive neural precursor (PRP) cells, as well as clonally expanded, progenitor or differentiated progeny cells thereof, and pharmaceutical compositions are also provided.

Methods of producing mammalian PDGF-responsive neural precursor (PRP) cells that optionally express PDGF receptor alpha, in vitro and in vivo, are provided. In one embodiment, a method includes culturing brain medial ganglionic eminence in a culture medium containing PDGF under conditions allowing clonal proliferation or differentiation of the PRP cells. In various aspects, a culture medium or administration does not include EGF or FGF2; a culture medium contains one or more of PDGF, thyroid hormone, BMP-2, CNTF, T3, PDGF, BDNF, NT-3 or FGF2.

In another embodiment, a method includes administering a PDGFR agonist to the mammal in an effective amount for delivery of the PDGFR agonist (e.g., PDGF) to increase PRP cell numbers. In one aspect, a mammal does not receive EGF or FGF. In additional aspects, a mammal is administered FGF2, BDNF or NT-3 substantially simultaneously with the PDGFR agonist. In another aspect, PDGFR agonist is administered locally, regionally or systemically, for example, to the brain (cranium) of the mammal. In various additional aspects, administration occurs intracranially, intravenously, intravascularly, intramuscularly, subcutaneously, intraperitoneally, topically, orally, nasally or by inhalation.

Methods of increasing oligodendrocytes, neurons or astrocytes in a mammal are also provided. In one embodiment, a method includes administering an effective amount of PDGFR agonist to the mammal to proliferate PRP cells; and administering an effective amount of thyroid hormone or T3 to increase oligodendrocytes, BMP-2 to increase neurons, or both BMP-2 and CNTF to increase astrocytes. In various aspects, FGF2, BDNF or NT-3 is administered substantially simultaneously with the PDGFR agonist to the mammal.

In a further embodiment, a method of producing oligodendrocytes includes culturing brain tissue from a mammal in a culture medium comprising a PDGFR agonist and allowing proliferation of PRP cells; and differentiating the proliferated PRP cells to produce oligodendrocytes, for example, by contacting the proliferated PRP cells with an effective amount of thyroid hormone or T3. In one aspect, the oligodendrocytes are contacted with an effective amount of BMP-2 and CNTF to produce neurons and astrocytes.

In a another embodiment, a method of producing neurons includes culturing brain tissue from a mammal in a culture medium comprising PDGFR agonist and allowing proliferation of PRP cells; and differentiating the proliferated PRP cells to produce neurons, for example, by contacting the proliferated PRP cells with an effective amount of BMP-2.

In an additional embodiment, a method of producing astrocytes, includes culturing brain tissue from a mammal in a culture medium comprising PDGFR agonist and allowing proliferation of PRP cells; and differentiating the proliferated PRP cells to produce astrocytes, for example, by contacting the proliferated PRP cells with an effective amount of BMP-2 and CNTF.

Methods of the invention include clonally expanding PRP cells. For example, PRP cells may be clonally expanded by contacting PRP cells with PDGF and FGF-2; or PDGF and BDNF; or PDGF and NT-3 prior to differentiating cells.

Administration in accordance with the invention includes intracranial, intravenous, intravascular, intramuscular, subcutaneous, intraperitoneal, topical, oral, nasal and inhalation. Mammals targeted for administration or in vivo delivery include humans, primates, murine, rattus, bovine, porcine, equine, avies, cavias, lagomorphs, canines and felines. Mammals include, for example, subjects in need of increased numbers of PRP cells, progenitor cells, oligodendrocytes, neurons or astrocytes, or progeny thereof. Mammals further include, for example, subjects suffering from a loss of or injury to oligodendrocytes, neurons or astrocytes; subjects' afflicted with or at risk of affliction with a neurological disease or disorder (e.g., affects central nerves, such as brain or spinal cord, or affects peripheral nerves, such as motor, sensory or autonomic nerves), or undesirable medical condition. Exemplary neurological diseases and undesirable medical conditions include neurodegenerative diseases, stroke (e.g., hemorrhagic stroke, focal ischemic stroke or global ischemic stroke), aneurysm, brain or spinal cord injury or cranium or spinal column trauma. Brain or spinal cord injury, or cranium or spinal column trauma, can be caused by a stroke or surgery.

Compositions and methods of the invention include inducing clonal proliferation or self-renewal of the PRP cells. In one embodiment, clonal proliferation or self-renewal is induced by contacting the PRP cells with PDGF and FGF-2; or PDGF and BDNF; or PDGF and NT-3. In another embodiment, a majority of the clonally proliferated cells are not differentiated into neurons, oligodendrocytes or astrocytes. In a further embodiment, a majority of the differentiated cells are neurons, oligodendrocytes, astrocytes or a combination thereof. Clonally expanded or self-renewed population of cells produced by the various methods are therefore also provided.

Methods for treating or ameliorating a disease, disorder or undesirable medical condition associated with neuron, oligodendrocytes or astrocyte loss, injury or dysfunction are provided. In one embodiment, a method includes transplanting an effective amount of the PRP cells or progeny thereof, to a mammal harboring the disease, disorder or medical condition. In another embodiment, a method includes administering an effective amount of PDGFR agonist to a mammal harboring the disease, disorder or medical condition, as well as one or more of FGF-2, thyroid hormone, T3, BMP-2 or CNTF. Methods of treatment additionally include embodiments that include administering one or more agents selected from PDGF; PDGF and FGF-2; PDGF and BDNF; PDGF and NT-3; thyroid hormone; T3; BMP-2; BMP-2 and CNTF.

Methods of treatment include treating a neurological injury or trauma, for example, which affects central or peripheral nerves (e.g., affects central nerves, such as brain or spinal cord, or affects peripheral nerves, such as motor, sensory or autonomic nerves). Exemplary neurological diseases and undesirable medical conditions include neurodegenerative diseases, stroke (e.g., hemorrhagic stroke, focal ischemic stroke or global ischemic stroke), aneurysm, brain or spinal cord injury or cranium or spinal column trauma. Brain or spinal cord injury, or cranium or spinal column trauma, can be caused by a stroke or surgery. Exemplary neurological diseases and undesirable medical conditions further include Alzheimer's Disease, multiple sclerosis (MS), macular degeneration, glaucoma, diabetic retinopathy, peripheral neuropathy, Huntington's Disease, amyotrophic lateral sclerosis (ALS), Parkinson's Disease, stroke, depression, epilepsy, neurosis and psychosis.

Methods of identifying agents that modulate clonal proliferation or self renewal or differentiation of a neural precursor cell are provided. In one embodiment, a method includes providing the PRP cells or progeny cells thereof; contacting the cells of step (a) with a candidate agent; and determining if the candidate agent modulates clonal expansion or differentiation of the cells. In one aspect, formation of progeny (e.g., neurospheres) is determined. In another aspect, differentiation into one or more of neurons, oligodendrocytes or astrocytes is determined.

DESCRIPTION OF DRAWINGS

FIGS. 6A-6D show data indicating that SHH signaling promotes generation of primary neurospheres by PRPs. A, PDGF-generated neurospheres in DMSO. B, cyclopamine reduces the size and numbers of PDGF-generated. Arrows illustrate normally differentiating cells, indicating the effect of cyclopamine is not due to toxicity. D, SHH signaling significantly enhances the generation or primary PDGF-generated neurospheres in comparison to PDGF alone. Scale bar in B is 100 μm.

DETAILED DESCRIPTION

Figure 1:
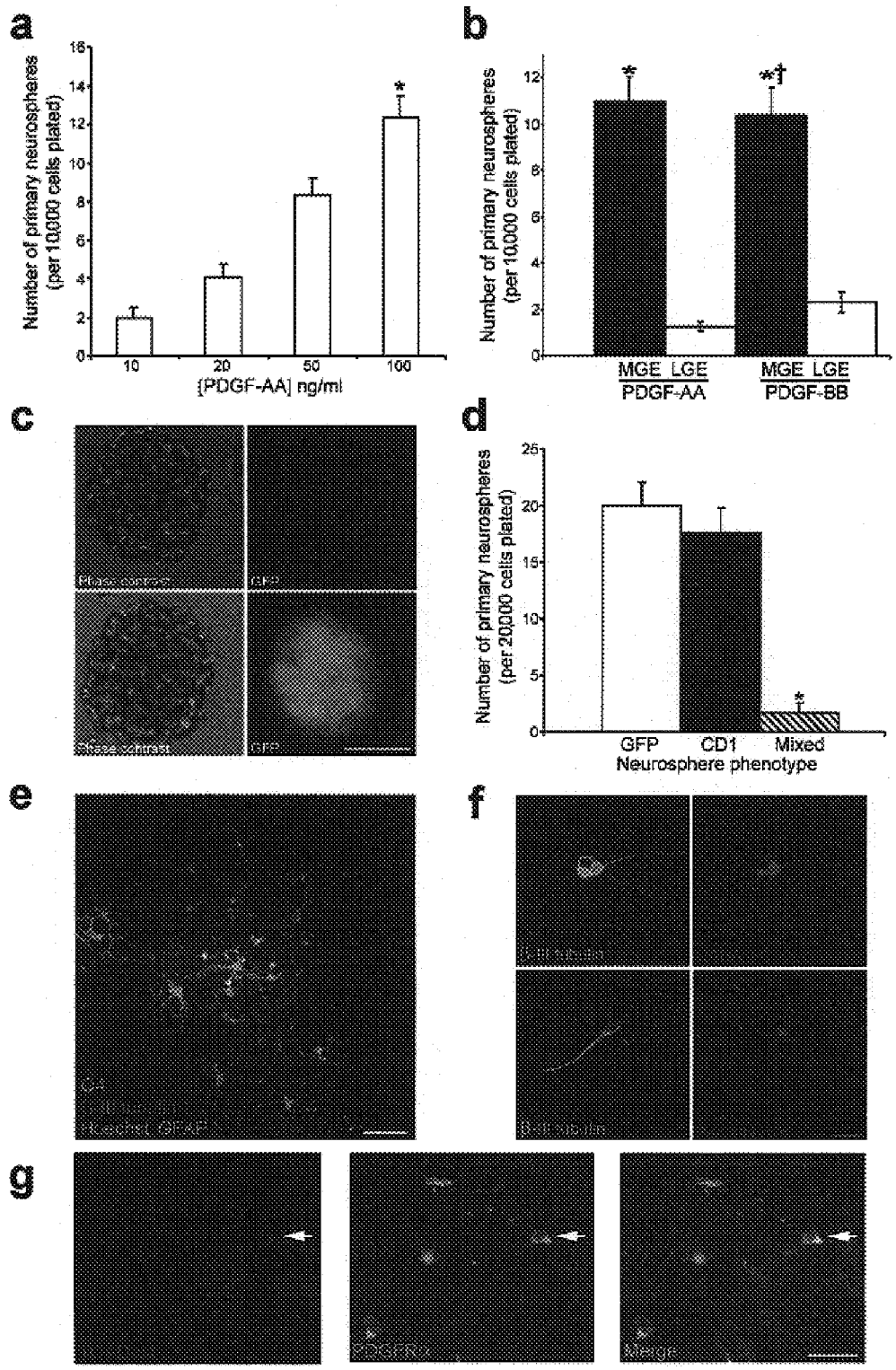
FIGS. 1A-1G show data indicating that PDGF induces proliferation of precursors from the MGE that can differentiate into neurons and oligodendrocytes. A, PDGF-AA induces generation of neurospheres in a dose-dependent manner. B, Significantly more neurospheres were generated from the MGE than the LGE by either PDGF-AA or PDGF-BB. C, D, GFP- and non-GFP-expressing dissociated E14 MGEs generated neurospheres not chimeric for GFP-expression, indicating clonal proliferation of PRPs. E, PDGF-generated neurospheres differentiated into oligodendrocytes and F, parvalbumin-immunoreactive GABA-ergic interneurons. G, Photomicrographs of PDGFRα-expressing precursor cells that co-express neuron-specific antigen TOAD-64 within the E14 forebrain. Scale bars for C, E, F, G are 50, 50, 25, and 25 μm, respectively.

The invention provides clonally-derived, self-renewing PRP cells. The invention also provides PRP progeny cells, including clonally-derived, self-renewing cells, progenitor cells, and differentiated cells. PRP cells have the capacity to generate neurons, oligodendrocytes, and astrocytes. PRP cells are distinct from cells generated by epidermal growth factor (EGF)-responsive neural stem cells (NSCs) in several respects. When differentiated in FBS, PRP progeny cells differentiate into neurons and oligodendrocytes, whereas EGF-generated progeny differentiate into neurons, oligodendrocytes, and astrocytes. PRPs are not self-renewing when passaged in EGF, whereas EGF NSCs are. Progeny cells of PRPs are highly motile in comparison to EGF-generated progeny.

PRPs are a neural precursor cell capable of forming progenitor cells or neurons and both types of macroglia during forebrain development. PRPs exhibit a limited capacity for self-renewal under conditions of passage with PDGF, which can be enhanced by fibroblast growth factor 2 (FGF2), a process dependent at least in part upon SHH. PRP cells may have an unlimited capacity for self-renewal when passaged with other factors or stimuli or under different conditions. PRP undergoes a series of symmetric and asymmetric cell divisions, to produce more of itself (self-renewal/clonal expansion) and a cell with the potential to differentiate into either a neuron or oligodendrocyte (N/O cell). In BMP-2 and CNTF, the majority of undifferentiated PRPs differentiate into astrocytes, which reduces the number of undifferentiated cells without affecting neuron numbers induced by BMP-2's action on the N/O cell. Astrocyte generation appears to be direct from PRPs and separate from the N/O cell because clones containing both astrocytes and oligodendrocytes are observed when PDGF-generated neurospheres are differentiated in triiodothyronine (T3) followed by the addition of BMP-2 and CNTF for the remainder of the differentiation period.

PRPs are a unique population of oligodendrocyte precursors, with both distinct and similar properties to other OLPs described previously (Liu et al., Trends Neurosci 26:410 (2003); Noble et al., Dev Bio 265:33 (2004); Rowitch, Nat Rev Neurosci 5:409 (2004)). PRPs are heterogeneous in their ability to generate neurons and subtypes of astrocytes. The development of OLPs suggests that OLPs in vivo are also a heterogeneous population. Even within the forebrain, based on the expression of TOAD-64 in PRPs, there appears to be heterogeneity. PRPs may maintain the capacity to generate neurons through to adulthood. Human PRPs generated as neurospheres permit isolating and expanding neural precursors or differentiated progeny for transplantation in white matter for the treatment of central nervous system (CNS) or peripheral nervous system (PNS) trauma, injury, a disease or disorder, or undesirable medical condition.

In accordance with the invention, there are provided isolated and purified mammalian platelet derived growth factor (PDGF)-responsive neural precursor (PRP) cells, wherein said cells express PDGF receptor alpha. In one embodiment, a cell, when contacted with one or more of thyroid hormone, bone morphogenetic protein-2 (BMP-2), ciliary neurotrophic factor (CNTF) or triiodothyronine (T3), gives rise to a differentiated neural cell that expresses detectable amounts of one or more protein markers selected from: GABA, parvalbumin, beta-II tubulin, calbindin D, calretinin, O4, neurofilament M (NFM), myelin basic protein (MBP), TOA-64/TUC-2 and GFAP. In another embodiment, a cell, when contacted with one or more of thyroid hormone, BMP-2, CNTF or T3, gives rise to a differentiated neuron, oligodendrocyte, astrocyte or mixture thereof. In an additional embodiment, at least a portion of cells give rise to a differentiated a neuron when contacted with BMP-2 and gives rise to a differentiated oligodendrocyte when contacted with triiodothyronine (T3). In a particular aspect, at least a portion of cells give rise to differentiated astrocytes when contacted with BMP-2 and CNTF. In another particular aspect, at least a portion of cells give rise to differentiated astrocytes when contacted with T3 followed by contact with BMP-2 and CNTF. In a further particular aspect, cells do not give rise to differentiated astrocytes by contact with BMP-2 alone or CNTF alone.

Further provided are cell intermediates that are progeny of an undifferentiated cell (e.g., PRP), but are not fully lineage committed or differentiated. In one embodiment, a cell is intermediate with respect to the mammalian PDGF-responsive neural precursor (PRP) cell and a neuron or oligodendrocyte, and the intermediate cell is designated an N/O cell, which can give rise to differentiated neurons or oligodendrocytes, but not astrocytes, when contacted with one or more of BMP-2 or T3.

In accordance with the invention, also provided are isolated and purified mammalian PDGF-responsive neural precursor (PRP) cell, wherein the cell expresses PDGF receptor alpha. In one embodiment, a cell exhibits greater clonal proliferation when contacted with a PDGF receptor (PDGFR) agonist and a fibroblast growth factor (FGF) receptor agonist, then when contacted with either PDGF alone or epidermal growth factor (EGF) alone. In another embodiment, a cell exhibits greater clonal proliferation when contacted with PDGF and brain derived neurotrophic factor (BDNF), then when contacted with either PDGF alone or EGF alone. In a further embodiment, a cell exhibits greater clonal proliferation under conditions of contact with PDGF and NT-3, then under conditions of contact with either PDGF alone or EGF alone. In an additional embodiment, a cell exhibits less clonal proliferation under conditions of contact with PDGF than clonal proliferation of neural stem cell (NSC) under conditions of NSC contact with EGF. Under different conditions, clonal proliferation may be different between PRP and NSC cells. In still further embodiments, a cell 1) does not form a neurosphere when contacted with PDGF alone, EGF alone or FGF2 alone; or forms a neurosphere when contacted with a PDGF receptor agonist and an FGF receptor agonist; or exhibits increased clonal proliferation when contacted with a PDGF receptor agonist and an FGF receptor agonist, as compared to clonal proliferation when contacted with PDGF alone, EGF alone or FGF2 alone. In various aspects of the embodiments set forth herein, clonal proliferation is induced or increased by stimulating sonic hedgehog signaling (SHH), and clonal proliferation is reduced or prevented by inhibition of sonic hedgehog signaling (SHH).

Additionally provided are cell cultures including undifferentiated and differentiated neural cells in varying proportions or cell numbers. In one embodiment, about ⅓ of the total number of cells in the culture comprise differentiated beta-III-tubulin expressing neurons, and differentiated astrocytes are fewer in number or absent; or about ⅓ of the total number of cells in the culture comprise differentiated beta-III-tubulin expressing neurons and about ⅓ of the total number of cells in the culture comprise differentiated oligodendrocytes, and differentiated astrocytes are fewer in number or absent; or differentiated astrocytes are present in the cell culture, and ⅓ or less of the total number of cells in the culture comprise differentiated neurons; or about ⅔ of the total number of cells in the culture comprise differentiated astrocytes, and ⅓ or less of the total number of cells in the culture comprise differentiated neurons. In another embodiment, at least 50%, 60%, 70%, 80% or more of total number of cells in the culture are neurons, oligodendrocytes or astrocytes. In various aspects of the embodiments set forth herein, neurons optionally express detectable amounts of parvalbumin or GABA.

As set forth herein, isolated and purified mammalian PDGF-responsive neural precursor (PRP) cells are distinct from neural stem cells (NSC). In one embodiment, a mammalian PDGF-responsive neural precursor (PRP) cell is more motile as compared to a progeny of EGF-responsive neural stem cell (NSC).

Isolated and purified mammalian PDGF-responsive neural precursor (PRP) cells include primary isolates from appropriate nerve tissue or organs (e.g., brain medial ganglionic eminence). Isolated and purified mammalian PDGF-responsive neural precursor (PRP) cells further include progeny cell or neurosphere of primary cell isolates.

Isolated and purified mammalian PDGF-responsive neural precursor (PRP) cells include cells that have been contacted with a factor or stimuli, or subjected to a condition, in vitro, ex vivo or in vivo. In one embodiment, a mammalian PDGF-responsive neural precursor (PRP) cell has been contacted with one or more of: PDGF, BDNF, NT-3, thyroid hormone, BMP-2, CNTF, EGF or T3.

Populations of clonally expanded or self-renewed mammalian PDGF-responsive neural precursor (PRP) cells, as well as undifferentiated progeny, progenitor progeny and differentiated progeny, wherein at least a portion of the cells expresses PDGF receptor alpha are additionally provided. In one embodiment, cells or progeny cells of the population have been contacted with a PDGFR agonist, an FGF receptor agonist, PDGF, BDNF, NT-3, thyroid hormone, BMP-2, CNTF, EGF or T3.

Mammalian PDGF-responsive neural precursor (PRP) cell as well as undifferentiated progeny, progenitor progeny and differentiated progeny, of various species and various developmental stages are provided. In various embodiments, a first, second, third, fourth, fifth, sixth seventh or subsequent generation progeny cell or cells (e.g., undifferentiated progeny, progenitor progeny and differentiated progeny) of mammalian PDGF-responsive neural precursor (PRP) cell is provided. In further embodiments, a cell is human, primate, murine, rattus, bovine, porcine, equine, avian, cavia, lagomorph, canine or feline, and is of embryonic, fetal, juvenile or adult origin.

Transformed mammalian PDGF-responsive neural precursor (PRP) cells, as well as undifferentiated progeny, progenitor progeny and differentiated progeny, are also provided. In one embodiment, a cell has been transformed with a nucleic acid (encoding a protein or a homologous recombinant construct). In particular aspects, a protein is selected from a neurotransmitter, neurotransmitter receptor, growth factor (e.g., nerve growth factor, brain-derived neurotrophic factor, neurotrophin, CNTF, amphiregulin, basic FGF, acidic FGF, EGF, transforming growth factor-alpha, transforming growth factor-beta, PDGF, insulin-like growth factor or interleukin), growth factor receptor (e.g., low affinity nerve growth factor receptor, CNTF receptor, neurotrophin receptor, EGF receptor, FGF receptor or amphiregulin receptor), neurotransmitter-synthesizing enzyme (e.g., tyrosine hydroxylase, tryptophan hydroxylase, phenylethanolamine N-methyltransferase, histidine decarboxylase, glutamic acid decarboxylase, choline acetyltransferase, dopa decarboxylase, dopamine beta hydroxylase or amino acid decarboxylase), neurotransmitter receptor-synthesizing enzyme, growth factor-synthesizing enzyme, growth factor receptor-synthesizing enzyme, or a neuropeptide (e.g., substance-P, neuropeptide-Y, enkephalin, vasopressin, vasoactive intestinal peptide, cholecystokinin, glucagon, bombesin, somatostatin, tachykinin, endorphin or calcitonin gene-related peptide).

In accordance with the invention, further provided are cell cultures including a PDGF-responsive neural precursor (PRP) cell that express PDGF receptor alpha. In one embodiment, a cell of the culture, when contacted with one or more of thyroid hormone, BMP-2, CNTF or T3, gives rise to a differentiated neural cell that expresses detectable amounts of one or more protein markers selected from: GABA, parvalbumin, beta-II tubulin, calbindin D, calretinin, O4, neurofilament M (NFM), myelin basic protein (MBP), TOA-64/TUC-2 and GFAP, and the cell of the culture is or has been contacted with one or more of PDGF, thyroid hormone, BMP-2, CNTF or T3. In another embodiment, a cell of the culture, when contacted with one or more of thyroid hormone, BMP-2, CNTF or T3, gives rise to a differentiated neural cell that expresses detectable amounts of one or more protein markers selected from: GABA, parvalbum in, beta-II tubulin, calbindin D, calretinin, O4, neurofilament M (NFM), myelin basic protein (MBP), TOA-64/TUC-2 and GFAP, and the cell of the culture is or has been contacted with one or more of PDGF, thyroid hormone, BMP-2, CNTF or T3 effective to increase expression of detectable amounts of one or more protein markers selected from: GABA, parvalbumin, beta-II tubulin, calbindin D, calretinin, O4, neurofilament M (NFM), myelin basic protein (MBP), TOA-64/C-2 and GFAP.

In accordance with the invention, additionally provided are cell cultures enriched for PDGF-responsive neural precursor (PRP) cells that express PDGF receptor alpha. In one embodiment, at least a portion of the enriched cells, when contacted with one or more of thyroid hormone, BMP-2, CNTF or T3, differentiate into a neural cell that expresses detectable amounts of one or more protein markers selected from: GABA, parvalbumin, beta-II tubulin, calbindin D, calretinin, O4, neurofilament M (NFM), myelin basic protein (MBP), TOA-64/TUC-2 and GFAP. In another embodiment, at least a portion of the enriched cells, when contacted with one or more of thyroid hormone, BMP-2, CNTF or T3, differentiate into a neuron, oligodendrocyte, astrocyte or mixture thereof.

As used herein, the term "isolated," when used to refer to a composition such as a cell means that the composition has been removed from it's naturally occurring environment. Such compositions need not be purified or homogeneous, but can be substantially free of other cell types or other cellular material with which it naturally occurs in the tissue of origin (e.g., neural tissue). Thus, for example, an isolated primary PRP neurosphere can be substantially free of connective tissue present in brain tissue or differentiated neural cells (e.g., neurons, oligodendrocytes, astrocytes, etc.). Accordingly, cells substantially free of connective tissue and cells dissociated from other cell or tissue types are further provided, wherein the cells have or have not been contacted with a PDGFR agonist.

Isolated compositions can be re-introduced into its naturally occurring environment after removal. For example, an isolated PRP cell can be removed, subject to clonal expansion, progenitor cell formation or differentiation, and be reintroduced (e.g., transplanted) into a subject.

As used herein, the term "purified," when used to refer to a composition such as a cell means that the composition has been separated from components with which it normally associated naturally occurring environment. A cell sample is considered "pure" when the sample has at least 60% or more cells (e.g., 65%, 70%, 75%, 80%, 85%, 90%, 95%, or more, 99%) than other cells of clonal origin.

As used herein, the term "enriched," when used to refer to a composition such as a cell means that the relative proportion of the composition has been increased as compared to the proportion of the composition prior to enrichment. For example, a PRP cell prior to enrichment may comprise 5% of the total cell number, but will comprise greater than 5% of the total cell number following enrichment.

Terms such as "stem cell," "precursor cell" and "progenitor cell" are commonly used in the art. The terminology used for undifferentiated neural cells has evolved such that these cells are referred to generally as "neural stem cells." Undifferentiated neural cells do have different characteristics and cell fates.

Totipotent stem cells can give rise to all cell types found in an embryo, fetus, or developed organism, including the embryonic components of the trophoblast and placenta required to support development and birth. The zygote and the cells at the very early stages following fertilization (i.e., the 2-cell stage) are considered totipotent.

Pluripotent stem cells are somewhat less plastic in their differentiative capacity than totipotent stem cells, but can become all cell types that are found in an implanted embryo, fetus, or developed organism. Unlike totipotent stem cells, pluripotent stem cells do not form embryonic components of the trophoblast or placenta.

The term "multipotent," when used in reference to a cell is a progeny of a stem cell within a particular tissue, organ, or physiological system. A multipotent stem cell is able to divide for many generations (the number of cell divisions may or may not be limited) under certain conditions and can give rise to daughter cells (typically, at least one is an undifferentiated cell) a proportion of which eventually terminally differentiates. As an example, a multipotent neural stem cell (NSC) is a cell that can undergo self-renewal or clonal expansion for many generations, and can eventually terminally differentiate into cell types that are normal components of the nervous system (e.g., cells present in CNS or PNS). Differentiated neural cells include neurons, oligodendrocytes and astrocytes.

A "neural precursor cell," as used herein, refers to an undifferentiated cell derived from a multipotent neural stem cell (NSC), but is not itself a stem cell. One distinguishing feature of a precursor cell is that, unlike a stem cell, it has a somewhat more limited self-renewal or clonal proliferative ability. Precursor cells can produce progeny that are capable of differentiating into more than one cell type.

PRP cells of the invention are neural cells that can be induced to proliferate as set forth herein under conditions that allow self-renewal or clonal proliferation. PRP cells can also terminally differentiate and give rise to different types of neural cells, oligodendrocytes, neurons and astrocytes, under appropriate conditions or stimuli, in vitro or in vivo. PRP cells can therefore be considered neural precursor cells.

A "progenitor cell," is an early descendant of a pluri-potent or multi-potent stem cell that can only differentiate, but typically does not undergo self-renewal or clonal expansion. In contrast, a stem cell or a precursor cell can renew itself (undergo cell division thereby making more stem cell progeny) or it can differentiate (undergo cell division and with each generation evolve into different types of cells). A progenitor cell is typically more limited into the kinds of cells it can give rise to than a stem or precursor cell. Progenitor cells are typically more differentiated than stem cells. Progenitor cells are also typically "lineage committed cell," which is a cell that is no longer pluripotent but has been induced to differentiate into one or more specific cell types.

Non-clonal progeny of neural stem cells and precursor cells include progenitor cells. The progenitor cells generated from a single multipotent neural stem cell are capable of differentiating into neurons, astrocytes and oligodendrocytes. As discussed, progenitor cells have little clonal proliferative ability and are typically committed to a particular path of differentiation and will, under appropriate conditions, eventually differentiate. An N/O cell has little if any clonal proliferative ability, but can differentiate into different neural cell types, namely neurons and ligodendrocytes and, therefore, can be considered a progenitor cell.

A "progeny" cell of any cells described herein refers to any and all first, second, third, fourth, fifth, sixth, seventh, eight, ninth, tenth, or any subsequent generation cell derived from a parental cell. Progeny of PRP cells include cells resulting from self-renewal/clonal proliferation or differentiation. Particular examples of progeny therefore include cells comprising neurospheres that form from primary PRP cells that undergo self-renewal/clonal proliferation. Additional particular examples of progeny include differentiated cells derived from neurospheres that form when PRP cells undergo cell division. Specific non-limiting examples of such differentiated progeny include neurons, oligodendrocytes and astrocytes. Progeny of PRP cells further include progenitor cells, which are cells intermediate in the developmental lineage between PRP cells and a differentiated cell. A specific non-limiting example of such a progenitor cell is an N/O cell.

As used herein, a "neurosphere" or "sphere," refers to a cluster of neural stem cells derived from a single parental neural cell. Neural cells comprising the neurosphere may be self-renewed or clonally proliferated progeny cells derived from a single parental cell. Under appropriate conditions or stimuli, neurospheres can typically be maintained for multiple passages in vitro without appreciable formation of fully differentiated progeny cells.

A "primary neurosphere" of PRP cells is produced from brain tissue in the presence of PDGF or other appropriate condition or stimuli. Primary neurospheres are generated from brain tissue without cell passaging. A "secondary neurosphere" is a neurosphere generated by dissociating (passaging) a primary neurosphere and culturing dissociated cells under conditions that result in formation of neurospheres from single cells. A "tertiary neurosphere" is a neurosphere generated by dissociating (passaging) a secondary neurosphere and culturing single dissociated cells under conditions that result in the formation of neurospheres from single cells, and so forth.

Neural cells comprising a neurosphere can give rise to precursor cells, progenitor cells or differentiated progeny cells derived from a single parental neural cell, in vitro or in vivo. For example, a differentiated progeny cell may comprise a cell that expresses a protein marker or has one or more morphological characteristics of a neuron, oligodendrocyte or astrocyte. Neural cells comprising a neurosphere may give rise to intermediate progeny cells with respect to the parental multipotent neural cell and a differentiated cell arising from the intermediate progeny. For example, an intermediate cell can be an N/O progenitor cell, which is intermediate between a PRP cell and differentiated progeny oligodendrocyte or neuron. In another example, an intermediate cell can be PRP cell, which is intermediate between an NSC cell and differentiated astrocyte. Neurospheres need not be a single cell type, but may comprise multiple precursor, intermediate (e.g., progenitor) or differentiated cells. For example, a neurosphere may comprise a population of PRP cells with or without any of N/O cells, neurons, oligodendrocytes or astrocytes.

Precursor cells, progenitor cells or differentiated progeny cells can arise in various proportions, depending upon the factors, conditions or stimuli to which the cells have been subjected to or treated, in vitro or in vivo. For example, for a differentiated cell, such as a neuron, oligodendrocyte or astrocyte, a plurality of progeny cells may comprise less or more than 10%, 20%, 30%, 40%, 50%, 60%, 70%, 80%, of neurons, oligodendrocytes or astrocytes, or cells that express a protein marker or has one or more morphological characteristics of a neuron, oligodendrocyte or astrocyte.

The term "cell culture" or "culture" refers to cells grown or maintained in an in vitro or artificial environment. A "cell culture" is a generic term that can also be used to encompass individual clonal cells, but also of groups of cells (e.g., neurospheres), progenitor cells, differentiated cells and mixtures thereof. A "cell culture medium," or "culture medium" are used interchangeably to refer to a nutritive composition intended to maintain viability of cells.

PRP cells can be obtained from embryonic, fetal, postnatal, juvenile or adult neural tissue. The neural tissue can be obtained from any animal that has neural tissue such as insects, fish, reptiles, birds, amphibians, mammals, etc. Typically, neural tissue suitable for obtaining PRPs is present in neural tissue of mammals, such as human and non-human primates, dogs, cats, rodents (mice, rats, guinea pigs) and rabbits. Neural tissue can be derived from the central nervous system, for example, the brain.

Non-human animals may be euthanized, and the neural tissue and specific area of interest removed using a sterile or non-sterile procedure. An area of particular interest is the ventral forebrain. The medial ganglionic eminence (MGE) is one area from which PRPs are present and can be obtained.

Human neural stem cells may be derived from embryonic or fetal tissue following elective abortion, or from a postnatal, juvenile or adult donor. Autologous neural tissue can be obtained by biopsy, or from a subject undergoing neurosurgery in which neural tissue is removed, for example, during epilepsy surgery, temporal lobectomy or hippocampalectomy.

PRP cells obtained from donor tissue can be dissociated. Cells can be dissociated using mechanical dissociation, as set forth in Example 1, or by other methods known in the art. Such methods include, for example, treatment with enzymes such as trypsin, collagenase. Dissociation of cells can be carried out in tissue culture medium (e.g., MHM). The cells can be cultured on a fixed substrate or in suspension. Cells plated on a fixed substrate typically have an initial density of about $1-5\times10^4$ cells/ml. Cells cultured in suspension have an approximate density of approximately $1\times10^4$ to $1\times10^5$ cells/ml.

PRP cells can be dissociated from other cells or tissue. For example, PRP cells can be substantially free of other neural or non-neural cell types present in the donor region, or free of connective tissue (connecting extracellular matrix).

Dissociated PRP cells can be maintained in culture medium capable of supporting cell growth, which can optionally include, supplements required for cellular metabolism, such as glutamine and other amino acids, vitamins, minerals and proteins such as transferrin and the like. Culture medium can also optionally include antibiotics to prevent contamination with bacteria, fungi (yeast, mold) or mycoplasm, such as penicillin, streptomycin, gentamicin, fungizone, etc. Culture conditions are at or near physiological conditions. The pH of the culture medium is close to physiological pH, typically between pH 6-8, or between about pH 7.0 to 7.8 (e.g., pH 7.4). Physiological temperatures range between about 30° C. to 45° C. Cells are typically cultured at temperatures between about 32° C. to about 42° C. (e.g., 37° C.).

The culture medium can be supplemented with factors, such as factors that modulate (increase or decrease) growth or proliferation and progeny formation. Such factors can be used to induce, promote or stimulate, or to prevent, decrease or inhibit progeny cell formation. Progeny cell formation includes clonal proliferation/self renewal, growth or proliferation or formation of intermediate (progenitor) cells, or growth or proliferation or formation of differentiated cells.

Non-limiting examples of such factors include "growth," "survival," or "mitogenic" factors which are molecules that alone or in combination with other factors can induce, promote or stimulate cell growth, survival, proliferation, differentiation, or tropism on cells or progeny thereof, in vitro or in vivo. Exemplary growth factors include platelet-derived growth factor (PDGF-AA, PDGF-BB and PDGF-AB), acidic fibroblast growth factor (aFGF or FGF-1), basic fibroblast growth factor (bFGF or FGF-2), brain-derived neurotrophic factor (BDNF), neurotrophin 3 (NT-3), EGF, SHH, amphiregulin and transforming growth factor alpha (TGFalpha). It is understood that functionally equivalent growth and survival factors are also considered to be included.

Platelet derived growth factor or PDGF is a protein factor which (1) shares substantial sequence identity with the native human PDGF; and (2) possesses a biological activity of the native human PDGF. Native PDGF consists of two polypeptide chains selected from Chain A and Chain B. Chain A and Chain B are similar. For example, the human Chain A and Chain B shares 56% sequence identity in the mature PDGF molecule. A PDGF molecule may consist of AA, AB or BB. A discussion of the structural and functional relationship of PDGF can be found, for example, in Hannink et al., *Biochem Biophys Acta* 989(1):1 (1989).

The term "substantial sequence identity," when used in reference to a protein, such as PDGF means there is sufficient sequence identity (e.g., at least one polypeptide that is at least about 30% identical with Chain A or Chain B of the native human PDGF at the amino acid level, or more, 40% or more at least about 60%, at least about 70%, and at least about 80% identical with Chain A or Chain B of the native human PDGF at the amino acid level) that the sequence retains a biological activity of PDGF. Thus, PDGF encompasses deletion, insertion, or substitution mutants of native human PDGF, provided such mutants retain at least a partial activity of native human PDGF. The term PDGF therefore encompasses PDGFs of other species, provided that the PDGF sequences retain at least a partial activity of native human PDGF. A representative "biological activity of PDGF" is binding to a PDGF receptor and stimulating tyrosine kinase activity of the receptor (Ek et al., *Nature* 295(5848):419 (1982); Nishimura et al., *Proc Natl Acad Sci USA* 79(14):4303 (1982)).

The term "percent identity" or "% identity," when used in reference to a protein, such as PDGF, refers to the percentage of amino acid sequence in Chain A or Chain B of the native human PDGF which are also found in the PDGF comparison sequence, when the two sequences are optimally aligned (including gaps). Percent identity can be determined by methods or algorithms known in the art, such as LALIGN or BLAST.

In addition to proliferation-inducing factors, growth factors that may be used (in culture medium or administered in vivo) in order to modulate cell survival, growth, proliferation or differentiation of cells include, for example, BMP-2, a thyroid hormone, triiodothyronine (T3), ciliary neurotrophic factor (CNTF), NGF, thyrotropin releasing hormone (TRH), transforming growth factor beta (TGFbeta) and insulin-like growth factors (e.g., $IGF_1$). It is understood that functionally equivalent growth factors are also considered to be included.

Further non-limiting examples of growth factors and other stimuli that can be used to modulate cell survival, growth or proliferation and progeny formation include FGF1, FGF-2, neurotrophin 4 (NT-4), interleukins, leukemia inhibitory factor (LIF), cyclic adenosine monophosphate, forskolin, tetanus toxin, high levels of potassium, glucocorticoid hormones (e.g., dexamethasone), isobutyl 3-methylxanthine, somatostatin, growth hormone and retinoic acid. These and other functionally equivalent growth factors and stimuli are applicable in the invention compositions and methods.

Growth factors can be used in amounts that provide the intended effect. In culture medium, typical amounts range between about 1 fg/ml to 1 mg/ml. Concentrations between about 1 to 100 ng/ml are usually adequate. Titration studies can be used to determine optimal concentration of a particular growth factor, or combination of factors.

Within about 3-4 days in a proliferation-inducing growth factor (e.g., PDGF), a PRP cell begins to divide giving rise to a cluster of undifferentiated clonal cells referred to as a "neurosphere." The cells of a single neurosphere are progeny of a single PRP cell and are clonal in nature. With continued appropriate culture conditions or stimuli, such as culturing in the presence of an appropriate growth factor (e.g., PDGF), cells within the neurosphere continue to divide and proliferate resulting in an increase in the size of the neurosphere and the number of clonal, undifferentiated cells therein. Under these conditions, PRP neurospheres do not appreciably differentiate and do not express detectable levels of one or more markers associated with differentiated neural cells, such as gamma-aminobutyric acid (GABA), paravalbumin, beta-II tubulin, neurofilament M (NFM), O4, myelin basic protein (MBP), and glial fibrillary acidic protein (GFAP). After about 4 to 5 days, proliferating neurospheres detach from the culture dish and appear as free-floating clusters characteristic of neurospheres.

Neurospheres can be dissociated to form single cells, counted and replated at the desired density and passaged to reinitiate self-proliferation and clonal expansion. A percentage of these dissociated cells form new neurospheres largely composed of undifferentiated cells. This procedure can be repeated for subsequent generation of secondary neurospheres, tertiary neurospheres, and so forth until the desired number of cells, or neurospheres, are obtained.

The process by which PRP cells grow and proliferate without appreciable differentiation is referred to herein as "clonal-expansion," or "self-renewal" and grammatical variations thereof. Clonal expansion refers to cells that proliferate from a single cell that are able to renew themselves for multiple generations in vitro under appropriate conditions or stimuli. Clonal expansion and self-renewal does not require that the cells be capable of propagation indefinitely. Such cells may be limited in the number of times they can be passaged before undergoing senescence.

Appreciable differentiation occurs when greater than 10-15% of the progeny cells are differentiated into a particular neural cell type, such as a neuron, oligodendrocyte or astrocyte, for a given round of cell-division, or generation. Appreciable differentiation does not refer to the presence of progenitor cells, since such cells are not considered differentiated.

PRP cells can be proliferated in vivo or in vitro. PRP progeny cells can be prepared by culturing appropriate brain tissue (e.g., MGE) in the presence of PDGF, but not EGF, FGF-2, or TGF. Clonal expansion can be increased or stimulated under appropriate conditions or stimuli. For example, administering a growth factor, or a combination of growth factors to a subject, or contacting cells in vitro or in vivo with a growth factor, or a combination of growth factors, or providing appropriate culture conditions or a stimulus. In particular, PDGF and FGF, PDGF and BDNF, and PDGF and NT-3, together, increase PRP clonal proliferation. Accordingly, cells can be proliferated in these and other functionally equivalent growth factors in order to increase or stimulate clonal expansion and formation of PRP cells or neurospheres. PRP cell differentiation can be induced as set forth herein. For example, BMP2—can be administered to or contacted with PRP cells in vivo or in vitro in order to give rise to neurons. T3 can be administered to or contacted with PRP cells in vivo or in vitro in order to give rise to oligodendrocytes. BMP2 and CNTF can administered to or contacted with PRP cells in vivo or in vitro in order to give rise to astrocytes.

Accordingly, factors can be added alone or in a combination with other factors, conditions or stimuli in order to produce PRP cells. Factors and the like can also be added in a temporal sequence (e.g., administration of, or contact with, a first growth factor, which influences expression of a second growth factor receptor, followed by administration of or contact with the second growth). For example, PRP cells can be contacted first with T3, followed by contact with BMP-2 and CNTF, which produces neurons and astrocytes.

Within about 2-3 days after PRP cells have been exposed to a factor or culture condition that can cause PRP cells to give rise to differentiated cells, PRP differentiated progeny begin to appear. Depending on factor(s) or culture condition, progeny cells express markers typically found on neurons, astrocytes or oligodendrocytes. Markers can be proteins or other molecules that are associated with or produced by one or more neural stem cells, precursor cells, progenitor cells or differentiated cells. The pattern of markers can be used to identify neural cell types and differentiation stage.

Exemplary cellular markers for neurons include parvalbumin, β-III-tubulin, gamma-aminobutyric acid (GABA), neuron specific enolase (NSE), NF and cytoskeletal protein MAP-2. Neurotransmitters, neurotransmitter receptors and enzymes that participate in neurotransmitter synthesis, deactivation (inhibition) or uptake are often expressed by neurons, which can be used as a marker to aid in identifying neurons.

Specific non-limiting examples of neurotransmitters include acetylcholine (ACh), dopamine, epinephrine, norepinephrine, histamine, serotonin or 5-hydroxytryptamine (5-HT), neuropeptides such as substance P, adrenocorticotrophic hormone, vasopressin or anti-diuretic hormone, oxytocin, somatostatin, angiotensin II, neurotensin and bombesin, hypothalamic releasing hormones such as TRH and luteinizing releasing hormone, gastrointestinal peptides such as vasoactive intestinal peptide (VIP) and cholecystokinin (CCK) and CCK-like peptide, opioid peptides such as endorphins like β-endorphin and enkephalins such as met- and leu-enkephalin, prostaglandins, amino acids such as inhibitory neurotransmitter gamma amino butyric acid (GABA), glycine, glutamate, cysteine, taurine and aspartate and dipeptides such as carnosine.

Specific non-limiting examples of neurotransmitter-synthesizing enzymes include glutamic acid decarboxylase (GAD) which is involved in the synthesis of GABA, choline acetyltransferase (CHAT) for ACh synthesis, dopa decarboxylase (DDC) for dopamine, dopamine beta-hydroxylase (DBH) for norepinephrine, and amino acid decarboxylase for 5-HT. Enzymes involved in deactivation or inhibition of neurotransmitters include acetyl cholinesterase (AChE), which deactivates ACh.

Enzymes involved in uptake of neurotransmitters into neuronal terminals include monoamine oxidase and catechol-o-methyl transferase for dopamine, for 5-HT, and GABA transferase for GABA. Neurotransmitter receptor markers include AChE nicotinic and muscarinic receptors, adrenergic receptors (e.g., alpha1, alpha2, beta1, beta2, etc.) and the dopamine receptor. Reliable markers useful for neuron identification include neuron specific enolase (NSE), NF, NeuN, and the neuron specific protein, tau-1.

Exemplary cellular markers for astrocytes include glial fibrillary acidic protein (GFAP). Type I astrocytes, which are differentiated glial cells that have a flat, protoplasmic/fibroblast-like morphology, are immunoreactive for GFAP but not A2B5. Type II astrocytes, which are differentiated glial cells that display a stellate process-bearing morphology, are immunoreactive for GFAP as well as A2B5.

Exemplary cellular markers for oligodendrocytes include NFM, MBP, O4 and galactocerebroside (GalC, a myelin glycolipid), a myelin glycolipid identifier. In temporal fashion, cells first become immunoreactive for O4, GalC and finally, MBP. Cells that do not express intermediate filaments specific for neurons or for astrocytes, typically express these oligodendrocyte markers. These cells also possess a characteristic oligodendrocyte morphology.

The presence of such markers can be assayed by various methods known in the art including, for example, immunocytochemistry. Antibodies to any of the aforementioned protein markers can be used in immunocytochemistry to identify the corresponding proteins. Immunocytochemistry (e.g. dual-label immunofluorescence and immunoperoxidase methods) utilizes antibodies that detect these proteins. In situ hybridization histochemistry can also be performed, using nucleic acid (e.g., cDNA or RNA) probes specific for the marker mRNA. Such in situ techniques can be combined with immunocytochemical methods to enhance identification of neural cell types. If desired, antibodies can be applied to Western and Northern blot procedures respectively to also aid in cell identification. Such techniques can be used to identify the cellular characteristics or determine phenotypic properties of neural cells such as neurons, astrocytes and oligodendrocytes. Such techniques can also be used to determine the effect of growth factors on the differentiating cells, as well as in screening and identification methods modulate can be determined.

In accordance with the invention, moreover provided are in vitro and in vivo methods of producing mammalian PDGF-responsive neural precursor (PRP) cells that express PDGF receptor alpha, via primary PRP cell isolation as well as progeny formation by clonal expansion or self-renewal, formation of progenitor cells, and formation of differentiated cells, as well as populations of cells produced by the various methods. In one embodiment, a method includes culturing brain ganglionic eminence (e.g., medial ganglionic eminence; MGE) in a culture medium containing PDGF under conditions allowing clonal proliferation or differentiation of the PRP cells. In various aspects, a culture medium does not contain EGF or FGF2; contains one or more of: PDGF, thyroid hormone, BMP-2, CNTF or T3; or contains one or more of: PDGF, BDNF, NT-3 or FGF2. In additional aspects, a method includes inducing clonal proliferation or self-renewal of the PRP cells (e.g., by contacting PRP cells with PDGF and FGF-2; or PDGF and BDNF; or PDGF and NT-3). In further aspects, a method includes inducing formation of PRP cell neurospheres (e.g., a majority of the clonally proliferated cells are not differentiated into neurons, oligodendrocytes or astrocytes). In additional aspects, a method includes inducing formation of differentiated neurons, oligodendrocytes, astrocytes, or a combination thereof.

In another embodiment, an in vivo method of increasing PRP cell numbers (e.g., in a mammal) includes administering a PDGFR agonist to an animal (e.g., in a mammal) in an effective amount for intracranial delivery of the PDGFR agonist (e.g., PDGF) to increase PRP cell numbers. In one aspect, an animal (e.g., mammal) does not receive EGF or FGF. In another aspect, an animal (e.g., mammal) is administered FGF2, BDNF or NT-3 substantially simultaneously with the PDGFR agonist to the mammal. In further aspects, administration is local, regional (brain) or systemic, intracranially, intravenously, intravascularly, intramuscularly, subcutaneously, intraperitoneally, topically, orally, nasally or by inhalation.

Methods of producing oligodendrocytes include, for example, in one embodiment, culturing brain tissue from a mammal in a culture medium with a PDGFR agonist and allowing proliferation of PRP cells; and differentiating the proliferated PRP cells to produce oligodendrocytes. In one aspect, a step is performed by contacting the proliferated PRP cells with an effective amount of thyroid hormone or T3. In another aspect, oligodendrocytes are contacted with an effective amount of BMP-2 and CNTF to produce neurons and astrocytes. In further aspects, proliferated PRP cells are clonally expanding by contacting said cells with PDGF and FGF-2; or PDGF and BDNF; or PDGF and NT-3 prior to a step.

Methods of producing neurons include, for example, in one embodiment, culturing brain tissue from a mammal in a culture medium with a PDGFR agonist and allowing proliferation of PRP cells; and differentiating the proliferated PRP cells to produce neurons. In one aspect, a step is performed by contacting the proliferated PRP cells with an effective amount of BMP-2. In other aspects, proliferated PRP cells are contacted with PDGF and FGF-2; or PDGF and BDNF; or PDGF and NT-3 prior to a step.

Methods of producing astrocytes include, for example, in one embodiment, culturing brain tissue from a mammal in a culture medium with a PDGFR agonist and allowing proliferation of PRP cells; and differentiating the proliferated PRP cells to produce astrocytes. In one aspect, a step is performed by contacting the proliferated PRP cells with an effective amount of BMP-2 and CNTF. In other aspects, proliferated PRP cells are expanded by contacted with PDGF and FGF-2; or PDGF and BDNF; or PDGF and NT-3 prior to a step.

In vivo methods include mammals in need of increased numbers of PRP precursor cells, progenitor progeny, or oligodendrocytes, neurons or astrocytes. Particular mammals include, for example, a mammal suffering from a loss of or injury to oligodendrocytes, neurons or astrocytes; a mammal afflicted with or is at risk of affliction with a neurological disease or disorder, or undesirable medical condition. Non-limiting examples of neurological diseases, disorders, and undesirable medical conditions include neurodegenerative disease, stroke, aneurysm, brain or spinal cord injury or cranium or spinal column trauma, which can be caused by a stroke or surgery. Non-limiting examples of stroke include hemorrhagic stroke, focal ischemic stroke and global ischemic stroke. Neurological disease or undesirable medical conditions can affect either central (e.g., brain or spinal cord) or peripheral nerves (e.g., one or more of motor, sensory or autonomic nerves).

Cells of the invention, including, for example, PRP cells, N/O cells and clonally expanded or differentiated progeny thereof, may be manipulated in order to produce modified forms. For example, PRP cells, N/O cells and clonally expanded or differentiated progeny thereof can be "transfected" or "transformed" with a nucleic acid. Nucleic acid can be introduced into such cells in vivo, ex vivo or in vitro. Such genetically modified cells into which nucleic acid has been introduced are conveniently referred to as transformed cells.

Transformed cells are useful in for expression of desirable proteins and can be used in accordance with the invention methods, for example, to treat, ex vivo or in vivo stroke, brain or spinal cord injury or trauma, a disease or disorder, or undesirable medical condition of CNS or PNS, among other methods of the invention. For example, PRP cells may be modified to express or to increase production of a biologically active substance such as a neurotransmitter or growth factor or the like. Transformed PRP cells can be clonally expanded or give rise to differentiated cells, as set forth herein.

The term "transformed," when used in reference to a cell (e.g., a PRP cell, or a clonally expanded or differentiated progeny thereof) does not only refer to the particular method or technique for producing the cell, but, rather, the nature of the cell itself, i.e., a cell that has been intentionally genetically modified. The nucleic acid may be stably or transiently expressed by the transformed cells. Transformed cells include progeny cells that are clonally expanded or have undergone self-renewal (e.g., PRP cells that maintain their non-differentiated state), intermediate cells (e.g., N/O cells), or differentiated cells (e.g., neurons, oligodendrocytes or astrocytes).

Once PRP cells are obtained, neurospheres can be optionally formed, cells dissociated into single cells, plated on petri dishes in culture medium and allowed to attach (e.g, overnight). Nucleic acid can be introduced into PRP cells to produce transformed cells. PRP cells can be differentiated into neural cells, e.g., neurons, oligodendrocytes or astrocytes, as set forth herein, prior to or following introduction of nucleic acid. Transformed PRP cells and clonally expanded/self-renewed progeny thereof have the capacity to differentiate to produce neurons, oligodendrocytes or astrocytes, as set forth herein. Such differentiated cell progeny are considered to also be within the meaning of a transformed cell.

Nucleic acid introduced into cells is typically part of a vector in which one or more expression control elements are operably linked to the nucleic acid of interest. Exemplary vectors include viral vectors, such as an adenovirus, adeno-associated virus (AAV), retrovirus (mammary tumor virus (MMTV), lentivirus), vaccinia virus including pSCII, Simian Virus 40 (SV40), paramyxovirus (measles virus), herpes virus, Rous Sarcoma Virus (RSV), or papilloma virus. The term "operably linked," when used in reference to the relationship between an expression control element and a nucleic acid means that the element regulates transcription or translation of the nucleic acid sequence. Expression control elements can be operably linked to nucleic acid in cis or in trans.

Control elements that modulate expression include viral and mammalian expression control elements. Specific non-limiting example include retroviral long terminal repeats (LTRs), simian virus 40 (SV40), cytomegalovirus (CMV); and mammalian cell-specific promoters (e.g., tyrosine hydroxylase).

A vector can include a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphotransferase, thymidine kinase (TK), and xanthin-guanine phosphoribosyltransferase (XGPRT). Such markers are useful for selecting stable transformants in culture.

Cells of the invention, including, for example, PRP cells, N/O cells and clonally expanded or differentiated progeny thereof, can have a targeted gene modification. Targeted gene modifications can be introduced via homologous recombination methods known in the art. For example, a homologous recombination vector can be prepared in which a gene of interest is flanked at its 5' and 3' ends by gene sequences that flank the endogenous genome in the target cell. Homologous recombination occurs between the gene of interest carried by the vector and the endogenous gene following introduction of the vector into the target cell. Methods for constructing homologous recombination vectors and homologous recombinant animals from recombinant stem cells are commonly known in the art (see, e.g., Thomas et al., *Cell* 51:503 (1987); Bradley, *Curr. Opin. Bio/Technol.* 2:823-29 (1991); and WO 90/11354, WO 91/01140 and WO 93/04169).

Methods for introducing nucleic acid into cells are known in the art. For example, a vector can be introduced using chemical, electrical or mechanical means such as liposomal or chemical mediated uptake of the nucleic acid. For example, a vector can be introduced by chemical transfection (DEAE dextran, calcium phosphate precipitation), electroporation, infection (e.g., recombinant viruses such as retrovirus, herpes-virus, adenovirus, adeno-associated virus, paramyxovirus), microinjection, a gene gun, cell fusion, liposomes, LIPOFECTIN™, lysosome fusion, synthetic cationic lipids, or a DNA vector transporter. A variety of methods for producing transformed cells are known in the art (see Maniatis et al., *Molecular Cloning: A Laboratory Manual, Cold Spring Harbor Laboratory, N.Y.* 1982).

Non-limiting examples of nucleic acid types that can be introduced into cells include sequences encoding proteins such as growth factors and growth factor receptors, survival factors and survival factor receptors, neurotransmitters and neurotransmitter receptors, and synthesizing or degrading (deactivating) enzymes. Specific examples of enzymes include those participating in the synthesis or deactivation of neurotransmitters, including amino acids, biogenic amines and neuropeptides. Additional non-limiting examples include reporter genes such as bioluminescent proteins, e.g., green fluorescent protein and luciferase, chloramphenicol acetyltransferase, β-galactosidase and β-lactamase.

PRP cells, N/O cells and clonally expanded, progenitor or differentiated progeny thereof that are genetically modified to produce a biological substance can be introduced into a subject. A biological substance can be one that is useful for treatment of a central nervous system (CNS) or peripheral nervous system (PNS) injury or trauma, a disease or disorder, or any undesirable medical condition in which there is a deficiency of the substance or a risk of deficiency, or where a subject may benefit from the substance or the cell that produces the substance.

For example, transformed cells that secrete a growth or survival factor (a peptide, mitogen, or other molecule that induces, stimulates, increases or promotes growth, survival, proliferation or differentiation) or a growth or survival factor receptor can be useful for treatment of CNS or PNS disorders. Exemplary growth factors include, but are not limited to, PDGF, NGF, BDNF, the neurotrophins (NT-3, NT-4/NT-5), CNTF, amphiregulin, thyroid hormone, T3, FGF1, FGF-2, EGF, TGFalpha, TGFbeta and insulin growth factors (IGFs). Exemplary growth factor receptors include, but are not limited to, p75 low affinity NGFr, CNTFr, the trk family of neurotrophin receptors (trk, trkB, trkc), EGFr, FGFr, and amphiregulin receptors.

Cells can be genetically modified to produce neurotransmitters or neurotransmitter receptors such as serotonin, L-dopa, dopamine, norepinephrine, epinephrine, tachykinin, substance-P, endorphin, enkephalin, histamine, N-methyl D-aspartate, glycine, glutamate, GABA, ACh, etc. Cells can also be genetically modified to produce neurotransmitter-synthesizing enzymes including, for example, TH, DDC, DBH, PNMT, GAD, tryptophan hydroxylase, ChAT, and histidine decarboxylase. Cells can additionally be genetically modified to produce neuropeptides including, for example, substance-P, neuropeptide-Y, enkephalin, vasopressin, VIP, glucagon, bombesin, CCK, somatostatin, calcitonin gene-related peptide, etc.

PRP precursor cells can be derived from transgenic animals. Such cells derived from transgenic animals are a priori genetically modified. Various methods for producing transgenic animals are known in the art. In an exemplary method, nucleic acid (e.g., DNA) is introduced into single-celled fertilized eggs by direct microinjection of DNA. Other methods include retroviral-mediated transfer, or gene transfer in embryonic stem cells. These and other techniques are described in Hogan et al., *Manipulating the Mouse Embryo, A Laboratory Manual* (Cold Spring Harbor Laboratory Ed., 1986).

Transformed PRP cells or clonally expanded progeny thereof can be implanted for cell/gene therapy into the CNS or PNS of a subject in need of the biological substance produced by the genetically modified cells. Alternatively, transformed cells can be subjected to a differentiation protocol in vitro prior to implantation. For example, transformed precursor cells can be differentiated using any of the protocols set forth herein. Once transformed cells have differentiated, they may be assayed for expression of the desired biological substance, or optionally directly implanted into a subject in need of the cells or biological substance expressed by the transformed cell.

Cells of the invention including PRP cells, progeny thereof including clonally expanded, progenitor or differentiated cells, and transformed cells, can be preserved or stored. For example, cryopreserved cells can be stored long term until they are needed. The cells can be suspended in an isotonic solution, such as a cell culture medium, containing a particular cryopreservant. Exemplary cryopreservants include dimethyl sulfoxide (DMSO) and glycerol. Cryopreservants are typically used at a concentration of 5-15%, usually about 8-10%, by volume. Cells are frozen and can be maintained at $-10°$ C., $-20°$ C. to $-100°$ C., (e.g., about $-70°$ C. to $-80°$ C.).

PRP cells and clonally expanded, progenitor or differentiated progeny, which are able to clonally proliferate and expand when maintained in appropriate culture conditions, have many desirable characteristics for cells to be used in transplantation of CNS or PNS. For example, PRP cells and clonally expanded, progenitor or differentiated progeny, have not been immortalized and are not of a tumorigenic origin. PRP cells and clonally expanded, progenitor or differentiated progeny, including transformed cells and progeny thereof, can therefore be used for transplantation into the same or a different heterologous, autologous, or xenogeneic host (subject). PDGF, other growth or survival factors, conditions or stimuli can be administered prior to, simultaneously with or following cell transplantation.

It is possible to prepare PRP cells from a subject's own nerve tissue (e.g. in the case of tumor removal via surgical resection or a biopsy). Neural stem cell progeny may be generated from dissociated tissue and proliferated in vitro. Expanded precursor cells may be genetically modified if necessary, and transplanted into the CNS or PNS of a subject. PRP cells and clonally expanded, progenitor or differentiated progeny can be administered to any subject in need of such cells, and in any manner.

PRP cells and clonally expanded, progenitor or differentiated progeny can be used to repair damage of tissues and organs resulting from injury, trauma, a disease or disorder, age, or any undesirable medical condition in which a subject may obtain a benefit. A subject can be administered a population of PRP cells or progeny thereof to regenerate or restore neural tissues or organs which have been damaged as a consequence of injury, trauma, a disease or disorder, age, or any undesirable medical condition in which a subject may obtain a benefit. A subject at risk of an injury, trauma, a disease or disorder, age, or any undesirable medical condition in which a subject may obtain a benefit can be administered a population of PRP cells or progeny thereof to prevent or inhibit injury, trauma, damage of neural tissues or organs which may be a consequence of injury, trauma, damage, a disease or disorder, age, or any other appropriate condition in which a subject may obtain a benefit. PRP cells and progeny thereof can therefore be used in neural tissue regeneration or a replacement therapy or protocol, ex vivo or in vivo.

PRP cells and progeny thereof can be used to provide biological substances to a subject in need thereof, i.e., a subject having a deficiency of the biological substance (e.g., a growth or survival factor, an enzyme, neurotransmitter, etc.), a subject at risk of having a deficiency of the biological substance, or a subject in which providing the biological substance will in turn provide the subject with some objective or subjective benefit. Suitable PRP cells and progeny thereof for invention methods therefore further include transformed cells, which can be used as a carrier to introduce a gene into a subject which will in turn provide the subject with some objective or subjective benefit.

In accordance with the invention, yet additionally provided, are methods of treating or ameliorating a disease, disorder or undesirable medical condition associated with insufficient numbers of or PRP loss, insufficient numbers of or neural progenitor cell loss, or insufficient numbers of or neuron, oligodendrocytes or astrocyte loss, injury or dysfunction. Methods of the invention include reducing progression, severity, frequency, duration, susceptibility or probability of the disease, disorder or undesirable medical condition associated with insufficient numbers of or PRP loss, insufficient numbers of or neural progenitor cell loss, or insufficient numbers of or neuron, oligodendrocytes or astrocyte loss, injury or dysfunction. In one embodiment, a method includes transplanting an effective amount of PRP cells, or any progeny thereof, to a mammal harboring the disease, disorder or medical condition. In various aspects, a method includes administering to a mammal one or more agents selected from PDGF; PDGF and FGF-2; PDGF and BDNF; PDGF and NT-3; thyroid hormone; T3; BMP-2; BMP-2 and CNTF. In another embodiment, a method includes administering an effective amount of PDGFR agonist to a mammal harboring the disease, disorder or medical condition, as well as one or more of FGF-2, thyroid hormone, T3, BMP-2 or CNTF.

Undesirable medical conditions include, for example, a neurological injury or trauma, that affects CNS (e.g., brain or spinal cord) or PNS (e.g., one or more of motor, sensory or autonomic nerves). Non-limiting examples of neurological injury or trauma include stroke, aneurysm, brain or spinal cord injury and cranium or spinal column trauma or injury. Non-limiting examples of types of stroke include hemorrhagic stroke, focal ischemic stroke or global ischemic stroke.

Specific non-limiting examples of diseases, disorders and undesirable medical conditions treatable in accordance with the invention include Alzheimer's Disease, multiple sclerosis (MS), macular degeneration, glaucoma, diabetic retinopathy, peripheral neuropathy, Huntington's Disease, amyotrophic lateral sclerosis (ALS), Parkinson's Disease, depression, epilepsy, neurosis and psychosis.

A "neural disease or condition associated with neuron or oligodendrocyte loss or dysfunction" is a disease or medical condition that is caused by or otherwise associated with neuron/oligodendrocyte loss or dysfunction. Examples of these diseases or conditions include neurological and neurodegenerative disorders and diseases, brain injuries or CNS or PNS dysfunctions. Neurodegenerative diseases include, for example, Alzheimer's Disease, multiple sclerosis (MS), macular degeneration, glaucoma, diabetic retinopathy, peripheral neuropathy, Huntington's Disease, amyotrophic lateral sclerosis, and Parkinson's Disease. Brain injuries include, for example, stroke (e.g., hemorrhagic stroke, focal ischemic stroke or global ischemic stroke) and traumatic brain injuries (e.g. injuries caused by a brain surgery or physical accidents). CNS dysfunctions include, for example, depression, epilepsy, neurosis and psychosis.

In the methods of the invention in which cells are delivered in vivo into a subject, a growth or survival factor (e.g., PDGF, BMOP-2, CNTF, thyroid hormone, T3, EGF, FGF, SHH, Bcl-2, etc.), condition or other stimuli can also be administered prior to, concurrently with, or following in vivo cell delivery. A microfabricated device or implant can also be used to deliver a growth or survival factor (e.g., PDGF, BMOP-2, CNTF, thyroid hormone, T3, EGF, FGF, SHH, etc.), condition or other stimuli prior to, concurrently with, or following in vivo cell delivery.

PRP cells and progeny thereof are also suitable for treating demyelination diseases. Undifferentiated PRP cells can be clonally expanded as set forth herein and injected into a demyelinated target region. The transplanted cells are expected to differentiate in vivo. Oligodendrocytes derived from PRP cells following proliferation or differentiation in vitro may be injected into demyelinated target regions in the subject.

Non-limiting examples of demyelination diseases include, for example, multiple sclerosis (MS), perivenous encephalomyelitis, neuromyelitis optica, concentric sclerosis, acute, disseminated encephalomyelitides, post encephalomyelitis, postvaccinal encephalomyelitis, acute hemorrhagic leukoencephalopathy, progressive multifocal leukoencephalopathy, idiopathic polyneuritis, diphtheric neuropathy, Pelizaeus-Merzbacher disease, neuromyelitis optica, diffuse cerebral sclerosis, central pontine myelinosis, spongiform leukodystrophy, and leukodystrophy (Alexander type).

Cells delivered in vivo, for example, via transplantation, can be delivered locally, regionally or systemically. Transplantation can be done in a manner in which particular neural tissues or organs, or regions of neural tissues or organs, are targeted. For example, specific brain regions which are affected by trauma, injury or stroke, neurodegenerative diseases, disorders or medical conditions, as set forth herein (e.g., Alzheimer's Parkinson's, aging, etc.) can be targeted for cell transplantation. Exemplary target area of brain include the subventricular zone, which is significantly reduced in aged mice. In addition, the subventricular zone is the source of olfactory neurons, and olfactory dysfunction is a hallmark of forebrain neurodegenerative diseases, such as Alzheimer's, Parkinson's and Huntington's diseases. An additional exemplary target area of brain includes basal ganglia (e.g., caudate and putamen), the nucleus basalis and the substantia nigra.

Cells are administered by any appropriate technique, such as injection, via a cannula, for example. Injection methods are known in the art (see, e.g., Duncan et al., *J Neurocytology*, 17:351 (1988); and in Neural Grafting in the *Mammalian CNS*, (Bjorklund and Stenevi, Eds. 1985)). Standard stereotactic neurosurgical methods can be used to inject cell suspensions into the brain or spinal cord.

Cells delivered in vivo in a subject can be examined for survival using various non-invasive scans such as computerized axial tomography (CAT scan or CT scan), nuclear magnetic resonance (NMR), magnetic resonance imaging (MRI) or positron emission tomography (PET). Examination of graft survival can be done by removing a section of neural tissue, and visually examining the affected region.

Cells delivered in vivo in a subject can also be identified by prior incorporation of detectable markers in the cells prior to transplantation. For example, tracer dyes such as rhodamine- or fluorescein-labelled microspheres, fast blue, bisbenzamide or histochemical markers such as the lac Z gene which produces beta galactosidase can be used to observe the cells and ascertain their survival, proliferation, differentiation, and so forth.

Activity or function of cells delivered in vivo can be assessed by using appropriate clinical indicia. For example, various functions including but not limited to endocrine, motor, cognitive and sensory functions can be ascertained in order to determine whether the cells delivered in vivo have activity or function in the subject. Motor tests include measuring movement, balance, coordination, akinesia or lack of movement, rigidity and tremors. Cognitive tests include various tests of ability to perform everyday tasks, as well as various memory tests.

An "effective amount" is an amount sufficient to achieve the intended purpose. In the methods of the invention in which a detectable result or beneficial effect is a desired outcome, such as a therapeutic benefit in a subject treated in accordance with the invention, cells can be administered in sufficient or effective amounts. An "amount sufficient" or "amount effective" includes an amount that elicits any desirable outcome for any duration of time and for any subjective or objective degree.

As used herein, an "amount sufficient" or "amount effective" refers to an amount of a PRP cells or progeny alone, or in combination with one or more other agents or therapeutic or treatment protocols or regimens set forth herein or appropriate for the disease, provides a long or short term detectable response, a desired outcome or beneficial effect in a given subject of any measurable or detectable degree or duration (e.g., for minutes, hours, days, months, years, or cured).

An amount sufficient or an amount effective can but need not be provided in a single administration and can but need not be administered alone (i.e., without a second drug, agent, treatment or therapeutic regimen or protocol), or in combination with another compound, agent, treatment or therapeutic regimen. In addition, an amount sufficient or an amount effective need not be sufficient or effective if given in single or multiple doses without a second compound, agent, treatment or therapeutic regimen, since additional doses, amounts or duration above and beyond such doses, or additional drugs, agents, treatment or therapeutic regimens may be included in order to be effective or sufficient in a given subject. An amount sufficient or an amount effective need not be effective in each and every subject, nor a majority of subjects in a given group or population. Thus, an amount sufficient or an amount effective means sufficiency or effectiveness in a particular subject, not a group or the general population. As is typical for such methods, some subjects will exhibit a greater or less response to a method of the invention, including treatment/therapy.

Reducing, inhibiting decreasing, eliminating, delaying, halting or preventing a progression or worsening or an adverse symptom of the condition, disorder or disease is a satisfactory outcome. The dose amount, frequency or duration may be proportionally increased or reduced, as indicated by the status of the condition, disorder or disease being treated, or any adverse side effects of the treatment or therapy. Dose amounts, frequencies or duration also considered sufficient and effective are those that result in a reduction of the use of another drug, agent, treatment or therapeutic regimen or protocol.

An "amount sufficient" or "amount effective" includes reducing, preventing, delaying or inhibiting onset, reducing, inhibiting, delaying, preventing or halting the progression or worsening of, reducing, relieving, alleviating the severity, frequency, duration, susceptibility or probability of one or more adverse or undesirable symptoms associated with the condition, disorder or disease of the subject. In addition, hastening a subject's recovery from one or more adverse or undesirable symptoms associated with the condition, disorder or disease is considered to be an amount sufficient or effective. Various beneficial effects and indicia of therapeutic benefit are as set forth herein and would be known to the skilled artisan.

An "amount sufficient" or "amount effective," in the appropriate context, can refer to therapeutic or prophylactic amounts. Therapeutically or prophylactically sufficient or effective amounts mean an amount that detectably improves the condition, disorder or disease, by one or more objective or subjective clinical endpoints appropriate for the condition, disorder or disease.

Methods of the invention therefore include providing a detectable or measurable beneficial effect or therapeutic benefit to a subject, or any objective or subjective transient or temporary, or longer-term improvement (e.g., cure) in the condition, disorder or disease. Thus, a satisfactory clinical endpoint is achieved when there is an incremental improvement in the subjects condition or a partial or complete reduction in the severity, frequency, duration or progression of one or more associated adverse symptoms or complications or inhibition, reduction, elimination, prevention or reversal of one or more of the physiological, biochemical or cellular manifestations or characteristics of the condition, disorder or disease.

A therapeutic benefit or improvement ("ameliorate" is used synonymously) therefore need not be complete ablation of any or all adverse symptoms or complications associated with the condition, disorder or disease but is any measurable or detectable objectively or subjectively meaningful improvement in the condition, disorder or disease. For example, inhibiting a worsening or progression of the condition, disorder or disease, or an associated symptom (e.g., slowing or stabilizing one or more symptoms, complications or physiological or psychological effects or responses), even if only for a few days, weeks or months, even if complete ablation of the condition, disorder or disease, or an associated adverse symptom is not achieved is considered to be beneficial effect.

As used herein, the term "subject" includes animals, typically mammalian animals, such as but not limited to humans, non-human primates (apes, gibbons, chimpanzees, orangutans, macaques), domestic animals (dogs and cats), farm animals (horses, cows, goats, sheep, pigs), birds and experimental animals (mouse, rat, rabbit, guinea pig).

Subjects include animal disease models (e.g., stroke, neurological injury or trauma, neurodegenerative diseases, disorders or undesirable medical conditions). Subjects include naturally occurring or non-naturally occurring mutated or non-human genetically engineered (e.g., transgenic or knockout) animals. Subjects further include animals having or at risk of having a disorder or disease as set forth herein.

Subjects having or at risk of having a disorder or disease or a condition appropriate for treatment as set forth herein include subjects with an existing condition or a known or a suspected predisposition towards developing a symptom associated with the condition, disorder or disease. Thus, the subject can have an active acute or chronic condition, disorder or disease, or a latent condition, disorder or disease. At risk subjects include those at risk or predisposed towards suffering from such conditions, disorders or diseases based upon genetic predisposition or a family history, detection of increased risk, or exhibit relevant correlating symptoms indicating predisposition or susceptibility, but the condition, disorder or disease may not presently manifest itself in the subject. Particular non-limiting examples of subjects include subjects having or at risk of having Alzheimer's Disease, multiple sclerosis (MS), macular degeneration, glaucoma, diabetic retinopathy, peripheral neuropathy, Huntington's Disease, amyotrophic lateral sclerosis and Parkinson's Disease, depression, epilepsy, neurosis and psychosis.

As used herein, the term "associated with," when used in reference to the relationship between a symptom and a condition, disorder or disease, means that the symptom is caused by the condition, disorder or disease, or is a secondary effect of the condition, disorder or disease. A symptom that is present in a subject may therefore be the direct result of or caused by the condition, or may be a secondary effect, for example, a subject reacting or responding to the condition, disorder or disease.

PRP cells and progeny thereof can be included in pharmaceutically acceptable carriers and excipients, i.e., pharmaceutical compositions. Pharmaceutical compositions can be delivered via any route, such as intracranially, intravenously, parenterally, intrathecally, intravascularly, intramuscularly, transdermally, intradermally, subcutaneously, intranasally, or intraperitoneally. Pharmaceutical compositions can be delivered into the central nervous system locally or regionally, for example, by injection or infusion. Alternatively, Pharmaceutical compositions can be delivered into the central nervous system systemically.

Pharmaceutical compositions can include a compound that facilitates traversal of the blood brain barrier. Blood brain barrier permeabilizers include, for example, bradykinin and bradykinin agonists (e.g., U.S. Pat. Nos. 5,686,416; 5,506,206 and 5,268,164).

Pharmaceutical compositions can be prepared by mixing cells with an appropriate vehicle suitable for the intended route of administration. Particular non-limiting examples of suitable carriers and excipients include artificial cerebral spinal fluid, and liquids compatible with maintaining cell viability. Liquid forms in which cells may be incorporated for administration include aqueous solutions.

Methods for screening and identifying modulators (agents, conditions or stimuli that modulate) of neural cell self-renewal/clonal expansion, progenitor progeny formation and differentiation are yet additionally provided. In one embodiment, a method of identifying an agent that modulates clonal proliferation or self renewal or differentiation of a neural precursor cell includes: providing PRP cells of or progeny cells thereof; contacting the cells with a candidate agent; and determining if the candidate agent modulates clonal expansion or differentiation of the cells. In various aspects, formation of neurospheres is determined. In additional aspects, differentiation into one or more of neurons, oligodendrocytes or astrocytes is determined.

Such screening and identification systems allow any agent, condition or stimuli to be screened for their ability to affect PRP or N/O cell self-renewal/clonal expansion or differentiation. Such an assay would include exposing PRP or N/O cells, as single cells, neurospheres, or mixtures (with or without progeny cells, intermediate cell or differentiated cells) to a particular agent (e.g., potentially bioactive substance), culture condition (varying cell density, substrate material or coating, feeder layers, growth medium type, conditioned or non-conditioned media, etc.), environmental stimuli (e.g., pH, temperature, hyper- or hypoxia), then determining whether that exposure modulated PRP or N/O cell self-renewal/clonal expansion or differentiation. Detection of a change in the rate, frequency or amount of self-renewal/clonal expansion or differentiation in the presence of the agent, culture condition, or environmental stimulus would identify that particular agent, culture condition, or environmental stimulus as a modulator of PRP or N/O cell self-renewal/clonal expansion or differentiation. For example, a change in PRP proliferation can be detected by an increase or decrease in the number of neurospheres that form or the size of the neurospheres.

Such methods for screening and identifying are not limited to pluripotent or precursor cells. In this regard, differentiated cells, including, for example, neurons, oligodendrocytes, and astrocytes may similarly be employed in the assay methods to identify a modulator of self-renewal/clonal expansion or differentiation.

Methods for screening and identifying modulators may be performed in solid phase, in solution, in culture (a primary cell isolate or cells in an in vitro culture medium, or any progeny cells thereof). Screening methods may be performed in vivo in appropriate animals, such as mice.

Any substance is appropriate for screening and identifying modulators. Particular non-limiting examples polypeptides and peptidomimetics, naturally occurring or recombinant, nucleic acids such as DNA or RNA. Non-protein molecules may be naturally occurring or chemically synthesized and include, for example, small organic compounds.

Unless otherwise defined, all technical and scientific terms used herein have the same meaning as commonly understood by one of ordinary skill in the art to which this invention relates. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

As used herein, the singular forms "a", "and," and "the" include plural referents unless the context clearly indicates otherwise. Thus, for example, reference to "a PRP cell or progeny cell" includes a plurality of PRP cells or progeny cells; and reference to "a symptom" includes a plurality of symptoms (e.g., adverse or undesirable). Of course, this does not preclude limiting certain embodiments of the invention to specific PRP cells or progeny cells, particular symptoms, particular conditions, disorders or diseases, particular subjects, etc., using appropriate language.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis disclosed herein. Thus, even though the invention is generally not expressed herein in terms of what the invention does not include, aspects that are not expressly included in the invention are nevertheless expressly or inherently disclosed herein. Furthermore, the invention includes embodiments which exclude subject matter that, in view of the subject matter and relevant technology, would be incompatible with one or more embodiments of the invention.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example provides a description of materials and methods.

Animals. TgN(GFPU)5Nagy (GFP) mice were obtained from Jackson Laboratory (Bar Harbor, Me.) and along with CD-1 mice stocks were maintained in the University of Calgary Bioscience Animal Resources Center.

Cell culture. The culture medium (MHM) was composed of DMEM/F-12 (1:1) including HEPES buffer (5 mM), glucose (0.6%), sodium bicarbonate (3 mM), glutamine (2 mM), insulin (25 µg/ml), transferrin (100 µg/ml), progesterone (20 nM), putrescine (10 µM), and sodium selenite (30 nM; all from Sigma, St. Louis, Mo., except glutamine from Invitrogen, Carlsbad, Calif.). The lateral, medial, or both ganglionic eminences (LGE, MGE or both) were removed from Embryonic Day 14 (E14) mouse embryos and mechanically dissociated with a fire-polished Pasteur pipette in MHM. Cells were plated at a density of $0.0 \times 10^6$ cells/ml unless otherwise indicated.

For neurosphere generation, PDGF-AA (100 ng/ml; Peprotech, Rocky Hill, N.J.), PDGF-BB (100 ng/ml; Peprotech), EGF (20 ng/ml; Peprotech), FGF2 (20 ng/ml; R&D [Minneapolis, Minn.])+heparan sulfate (2 µg/ml; HS; R&D), SHH (2 ug/ml; R&D), cyclopamine (5 µM; Toronto Research Chemicals, North York, Ontario), and/or DMSO (0.1%; carrier) was added to the MHM. MHM used to generate neurospheres also contained 2% B27 (Invitrogen).

Neurospheres were differentiated on poly-L-ornithine coated coverslips in MHM and in the presence or absence of 1% FBS (Invitrogen), BMP-2 (Genetics Institute; Cambridge, Mass.), T3 (Sigma), and/or CNTF (generated as previously described (Gupta et al., *J Neurobiol* 23:481 (1992)) for 2 to 3 DIV. In order to determine whether PDGF-induced neurosphere generation was the result of clonal expansion, dissociated E14 MGEs from GFP and CD1 albino mice and were cultured in PDGF-AA, 1:1, at a density of $0.02 \times 10^6$ cells/ml for 6 DIV. The number of GFP, non-GFP, and chimeric GFP expressing neurospheres were counted after 6 DIV using a Leica Microsystems DMIL inverted fluorescence microscope (Richmond Hill, ON).

Self-renewal capacity was examined by single sphere dissociation. Briefly, single 6 DIV neurospheres of equivalent size that were generated in the presence of EGF, PDGF-AA, or PDGF-AA and SHH were transferred into 96 well plates and mechanically dissociated. Dissociates were cultured in MHM supplemented with EGF, FGF2 (includes 2 µg/ml HS), FGF2 and SHH, PDGF-AA, PDGF-AA and SHH, PDGF-AA and FGF2, PDGF-AA and FGF2 and SHH, PDGF-AA and DMSO (0.1%), PDGF-AA and SHH, or PDGF-AA and FGF2 and cyclopamine. The number of secondary neurospheres generated was counted after 9 DIV.

To determine if extrinsic factors could promote self-renewal of PRPs, individual, 7 DIV, GFP-expressing, PDGF-generated neurospheres were isolated, dissociated in the presence of PDGF-AA, and differentiated on coverslips that had been plated 2 days earlier with or without $0.2 \times 10^6$ cells/ml of EGF-generated cells from dissociated primary EGF neurospheres. EGF-generated feeder cells had been allowed to differentiate for 2 days in the presence of 1% FBS. Plates were rinsed 3× with MHM prior to the addition of GFP-expressing, PDGF-generated dissociates. Numbers of adherent clones and cells per clone were assessed by GFP expression. All images were captured with a Photometrics Coolsnap digital camera (Tuscon, Ariz.) mounted on a Leica Microsystems DMIL inverted fluorescence microscope with Coolsnap V1.2.0 software.

Immunofluorescence. Six DIV primary PDGF-AA-generated neurospheres were differentiated on poly-L-ornithine coated coverslips and after 2 DIV were fixed for 20 min. in 4% paraformaldehyde. For mouse IgM anti-O4 (1:10; Chemicon; Temecula, Calif.), coverslips were incubated in PBS (pH 7.5) overnight at 4° C. Coverslips were also incubated with mouse anti-β-II-tubulin (Sigma; 1:1000), rabbit anti-GFAP (BTI, Stoughton, Mass.; 1:300), mouse anti-GFAP (Chemicon 1:500), goat anti-mouse PDGFRα (1:10; R&D), rabbit anti-GFP (1:100; Santa Cruz; Santa Cruz, Calif.), rabbit anti-Human MBP (1:200; DAKO; Mississauga, ON), mouse anti-neurofilament M (1:50; RMO270; gift from Dr. Virginia Lee), and/or rabbit anti-OLIG2 (1:250) in 0.3% Triton-X-100 in PBS for 2 hours at 37° C. After incubation with primary antibodies, all tissue was incubated for 1 hour in PBS and 10% normal serum of the secondary antibody host (all secondary antibodies and reagents from Jackson Immunoresearch, except for HRP-conjugated secondary from Chemicon). This was followed by a 1-hour incubation with a biotin-conjugated secondary antibody and afterwards a 1-hour incubation at 37° C. with streptavadin-Cy3 (1:1000) or streptavadin-FITC (1:500) for O4 staining. For the other primary antibodies, the coverslips were incubated with the appropriate secondary antibody and/or Hoechst 33258 (1:100-1000; Sigma).

The neuronal phenotypes of PDGF-AA generated progeny were examined in 6 DIV neurospheres differentiated in 1% FBS for 2 DIV or on E14 dissociated whole brains plated on poly-L-ornithine coated coverslips for 5 DIV in the presence of 1% FBS. Coverslips were incubated overnight at 4° C. in rabbit anti-rat parvalbumin (1:1000; Swant; Bellinzona, Switzerland), rabbit anti-mouse GABA (1:500; Sigma), rabbit anti-mouse calretinin (1:1000; Swant), mouse anti-mouse calbindin-D (1:200; Sigma) and/or mouse anti-β-III-tubulin. Coverslips were then incubated with appropriate secondary antibodies as above.

For immunohistochemistry on cryosections, E14 brains were dissected out and processed as previously described (Shimazaki et al., *J Neurosci* 21:7642 (2001)). For staining with rabbit anti-mouse PDGFRα (Santa Cruz), transverse sections (10 µm) were first incubated in 1% $H_2O_2$ in PBS for 30 minutes at RT. Subsequently, sections were incubated with the antibody (1:300) in 0.3% Triton X-100, 10% normal goat serum in PBS overnight at RT. Sections were then washed and incubated with the appropriate horseradish peroxidase-conjugated secondary antibody for 1 hour at RT. Sections were then incubated with 3,3'-diaminobenzidine (Sigma; 1×10 mg tablet in 20 ml of PBS and 10 µl of 30% $H_2O_2$) 10 minutes or until the desired intensity of reaction product was reached. For double labeling, E14 brains were fixed as above, and 10-15 µm transverse sections were cut on a vibratome (Leica), mounted onto slides, and were incubated with sheep anti-mouse EGFR (1:50; Biodesign International, Kennebunk, Me.), or rabbit anti-mouse FGFR2 (1:50; Santa Cruz) in PBS. This was followed by washes and incubation with the appropriate biotin-conjugated secondary antibodies for 2 hours at RT. Sections were then washed and incubated with streptavadin-cy3 (1:1000), followed by a 2-hour incubation at 37° C. with goat anti-mouse PDGFRα (1:10; R&D) in 0.3% triton X-100 in PBS. After washes in PBS, sections were incubated for 1 hour with the appropriate secondary antibody. All immunofluorescent slides were mounted with Fluorsave (Calbiochem; San Diego, Calif.). Images were captured with a Photometrics Quantix camera or an Axiocam (Zeiss; Thornwood, N.Y.) mounted on a Zeiss Axioplan2.

Example 2

This example includes data indicating that E14 medial ganglionic eminence (MGE) is the source of neurosphere generating PRPs. This example also includes data indicating that PRPs have potential to differentiate into neurons and oligodendrocytes PDGFR-AA is one of the earliest markers of OLPs, and signaling by PDGF-AA is required for the generation of most oligodendrocytes (Fruttiger et al., *Development* 126:457 (1999)). Increasing concentrations of PDGF-AA were used to determine whether stimulation of dissociated E14 medial and lateral ganglionic eminences. (MGE and LGE, respectively) results in generation of neurospheres. The neurosphere assay was used because manipulation of primary cells is minimal compared to the immunopanning procedures used to isolate O-2A progenitors.

PDGF-AA induced neurosphere production in a dose-dependent manner. Significantly more neurospheres were produced in 100 ng/ml of PDGF-AA compared to all other concentrations tested ($p<0.01$; $12\pm1$ neurospheres per 10,000 plated cells; Tukey HSD; n=3) (FIG. 1A).

Expression of PDGFRα is largely restricted to the MGE at E14 (Tekki-Kessaris et al., *Development* 128-2545 (2001)). If endogenous PRPs were being isolated then their generation should be restricted to the MGE. The studies indicate that the MGE produced significantly more neurospheres (>4-fold; FIG. 1B) than the LGE with either PDGF-AA or PDGF-BB ($p<0.0001$; t test; n=4 and n=3, respectively), corroborating that endogenously generated PRPs were in fact isolated from MGE.

PDGF is also known to have chemotaxic effects on cortical NSCs (Forsberg-Nilsson et al., *J Neurosci Res* 53:521 (1998)), and thus it was possible that neurospheres generated under PDGF stimulation resulted from the directed migration of NSCs along the culture dish into clumps that resembled clonally-derived neurospheres. This possibility was studied, as previously described (Represa et al., *Eur J Neurosci* 14:452 (2001)), by culturing dissociated E14 MGEs from CD1 and TgN(GFPU)5Nagy (ubiquitous green fluorescent protein [GFP]-expressing) mice together, 1:1, at 20,000 cells/ml, and in the presence of 100 ng/ml of PDGF-AA. If cell clumping generates the majority of the neurospheres, then most neurospheres should contain both GFP- and non-GFP-expressing cells. However, $95\pm11\%$ of the neurospheres were not chimeric for GFP expression ($p<0.01$; Tukey HSD; n=3) (FIGS. 1C-D), and there was no difference in the number of GFP- or non-GFP-expressing neurospheres produced ($p>0.65$; Tukey HSD; n=3) (FIG. 1D). Together, the data indicate that neurospheres generated by PDGF stimulation are products of clonal cell proliferation.

The phenotype potential of the PDGF-generated neurospheres was examined with indirect immunocytochemistry using antibodies directed against GFAP (astrocytes), β-III-tubulin (neurons), and O4 (oligodendrocytes). PDGF-generated neurospheres differentiated into neurons and/or oligodendrocytes, but not astrocytes, after 2 DIV in the presence of 1% FBS (FIG. 1E).

The MGE largely gives rise to interneurons that migrate out towards the cortex, in a manner similar to OLPs (Marin et al., *Nat Rev Neurosci* 2:780 (2001)). To determine if PDGF-generated neurons, which are MGE-derived, expressed interneuronal antigens, immunocytochemistry with antibodies directed against GABA, calbindin D, calretinin and parvalbumin, was used to examine the phenotype of the differentiated neurons (after 2 DIV in the presence of 1% FBS) from 6 DIV PDGF-AA-generated neurospheres. The studies indicate that all antigens were detected in E14 dissociated whole brains differentiated for 5 DIV. However, differentiated neurons from PDGF-AA-generated neurospheres, identified by β-III-tubulin immunoreactivity, expressed only GABA or parvalbumin (FIG. 1F). These findings are in agreement with transplantation studies by Wichterle et al., *Development* 128: 3759 (2001), which demonstrated that over 70% of the neurons derived from the MGE differentiated into parvalbumin-immunoreactive, GABAergic interneurons.

To determine if neurons clearly differentiated from the progeny of PRPs in vivo, co-expression of neuronal antigens in PRPs in vivo was ascertained. PDGFRα-immunoreactive cells within the E14 MGE were also immunopositive for TOAD-64/TUC-2 (Minturn et al., *J Comp Neurol* 355:369 (1995)), an early neuron-specific antigen (FIG. 1G). Together, the data indicate that PRPs contribute, in addition to oligodendrocytes, to the generation of neurons within the forebrain.

Example 3

This example includes data indicating that PRPs are distinct from EGF-responsive NSCs.

The finding that PRPs reside mainly in the MGE, and that they do not produce astrocytes, indicate that PRPs are distinct from EGF-responsive NSCs. Indeed, EGF can generate neurospheres from both MGE and LGE, and these neurospheres produce neurons, oligodendrocytes, and astrocytes when differentiated in 1% FBS (Reynolds et al., *Dev Biol* 175:1 (1996)). If PDGF and EGF stimulate distinct populations to produce neurospheres, one would predict a predominantly non-overlapping pattern of PDGF and EGF receptor expression within the MGE or anterior entopeduncular (AEP). Thus, the expression of PDGFRα and EGFR was studied in transverse sections of the E14 forebrain.

Figure 2:
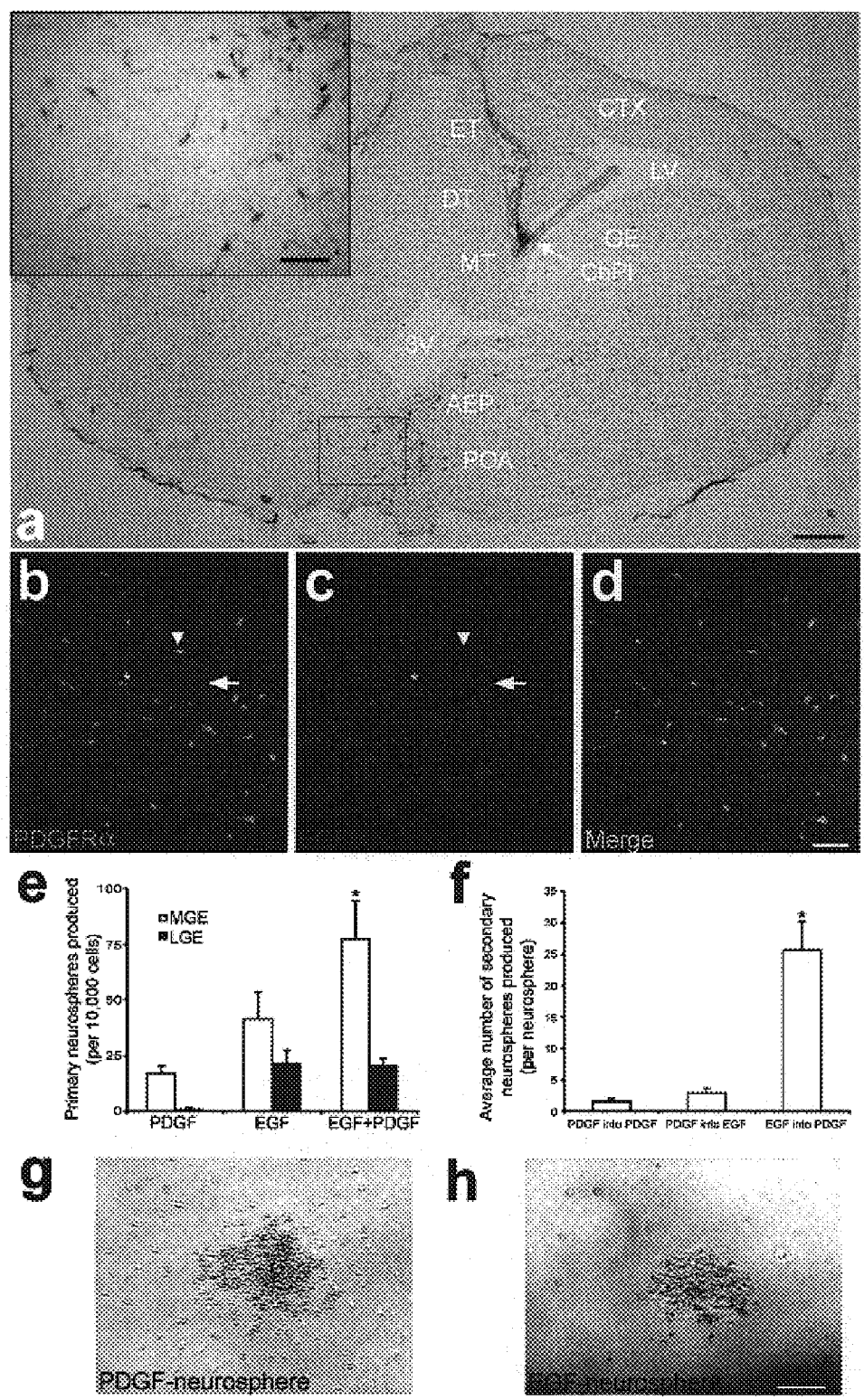
FIGS. 2A-2H show data indicating that PRPs are distinct from EGF-responsive NSCs. A, Low power photomicrograph illustrating PDGFRα within the AEP (inset), as well as in the primordium of the choroid plexus (arrow). High power photomicrographs of B, PDGFRα- and C, EGF receptor-expressing separate precursor populations (merged, D). E, Greater numbers of neurospheres generated in PDGF-AA and EGF compared to PDGF-AA or EGF alone. F, PRPs have a limited self-renewal capacity when single neurospheres of the same size were passaged in PDGF or EGF compared to EGF-generated neurospheres passaged in PDGF. G, PDGF-generated differentiated progeny migrated large distances away from the center of differentiating neurospheres in comparison to H, EGF-generated neurospheres, which were rarely seen migrating away from neurospheres. Scale bars for A, inset in A, D, and H are 200, 50, 50, and 100 μm, respectively. Asterisks in B and C indicate autofluorescent blood cells.

PDGFRα expression was largely restricted to the AEP, preoptic area, the primordia of the choroid plexus, and the meninges (FIG. 2A). Double-labelling for PDGFRα (arrowhead) and EGFR (arrow) revealed two populations of cells that were non-overlapping in their expression of these receptors (FIG. 2B-D).

Tropepe et al., *Dev Biol* 208:166 (1999), found that embryonic EGF and FGF NSCs were two distinct cell populations, by virtue of their generation of neurospheres being additive under clonal conditions. Thus, if PRPs and EGF-responsive NSCs are truly different populations as indicated by the expression patterns of their receptors, the generation of neurospheres with both PDGF-AA and EGF should also be additive. Accordingly, cells from the LGE or MGE were cultured (10,000 cells/ml) in the presence of 100 ng/ml of PDGF-AA, 20 ng/ml of EGF, or both, and the resultant primary neurospheres were counted. Dissociated MGEs cultured in the presence of EGF and PDGF-AA produced significantly more neurospheres than MGEs cultured in either EGF or PDGF-AA alone (FIG. 2E; $p<0.05$; LSD test; n=4). In contrast, there was no difference in the number of neurospheres produced from dissociated LGEs cultured in the presence of EGF and PDGF-AA in comparison to EGF alone ($p>0.86$; LSD test; n=4).

Primary EGF-generated neurospheres, when dissociated and cultured in EGF, always produce many secondary neurospheres (Reynolds et al., *Dev Biol* 175:1 (1996)), indicative of their extensive self-renewal capacity. PRPs were therefore studied for a similarly extensive capacity for self-renewal. Single, primary PDGF-generated neurospheres produced almost no secondary neurospheres ($1\pm1$) when mechanically dissociated in 96-well plates containing PDGF-AA (FIG. 2F, n=7, 69 neurospheres examined [NE]). Primary PDGF-generated neurospheres passaged into EGF (n=3, 32 NE), also produced very few ($3\pm1$) secondary neurospheres. In contrast, primary EGF-generated neurospheres processed in the same manner, but passaged into PDGF-AA (*$p<0.0001$; Tukey HSD; n=3, 24 NE) produced $26\pm5$ secondary neurospheres. Thus, unlike EGF NSCs, which have the capacity to passage into EGF or PDGF-AA, primary PRPs rarely self-renew in either PDGF-AA or EGF.

To determine whether there were differences in the differentiation of both types of neurospheres, primary 6 DIV EGF- and PDGF-AA-generated neurospheres were plated for 24 hours on poly-L-ornithine coated coverslips. Within 24 hours of plating, PDGF-AA-generated progeny migrated great distances (over 300 μm in some instances) from the center of neurospheres (FIG. 2G). In contrast, primary EGF-generated progeny rarely migrated away from the center of differentiating neurospheres (FIG. 2H). Together these data demonstrate that PRPs are a population distinct from that of EGF-responsive NSCs.

Example 4

This example includes data indicating that BMP-2 and T3 promote differentiation of PRP into neurons and oligodendrocytes, respectively.

Figure 3:
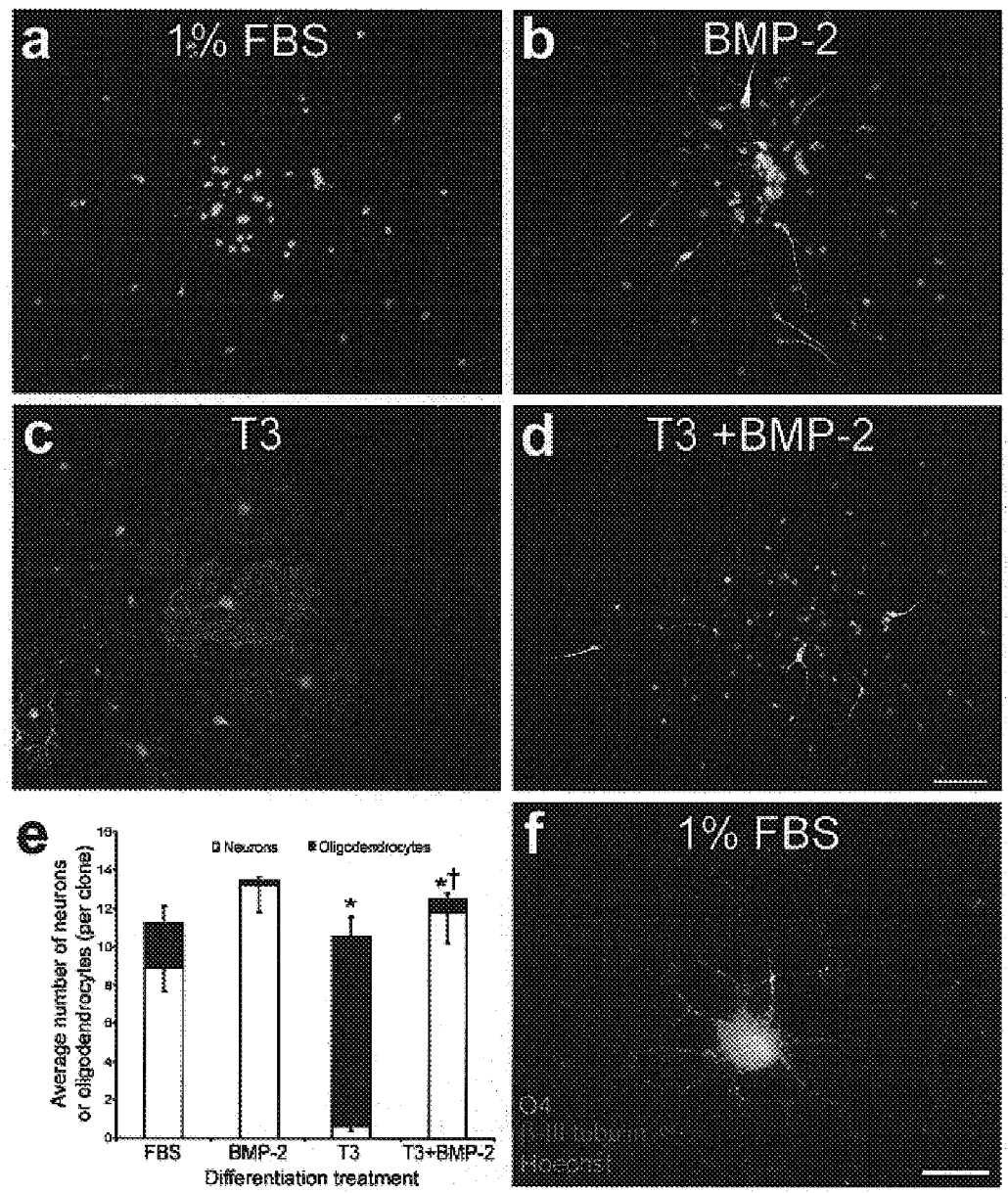
FIGS. 3A-3F show data indicating that BMP-2 and T3 promote differentiation of neurons and oligodendrocytes from PDGF-generated neurospheres, respectively. Primary PDGF-AA-generated neurospheres differentiated for 2 DIV in A, 1% FBS; B, BMP-2; C, T3; or D, T3 and BMP-2 analyzed for immunocytochemistry against β-III-tubulin (neurons), O4 (oligodendrocytes), and Hoechst (nuclei, blue); and E, numbers of immunoreactive cells. F, cells in 1% FBS with an oligodendroglial morphology express both O4 and β-III-tubulin. Scale bars in D and F are 50 μm and 12.5 μm, respectively.

BMP and T3 direct astroglial and oligodendroglial differentiation of O-2A progenitors, respectively (Ahlgren et al., *Mol Cell Neurosci* 9:420 (1997); Mabie et al., *J Neurosci* 17.4112 (1997)). To determine whether BMP-2 and T3 could direct differentiation of cells within PDGF-generated neurospheres, six DIV primary PDGF-AA-generated neurospheres were differentiated on coverslips for 2 DIV, in 10% FBS, 50 ng/ml of BMP-2, 20 ng/ml of T3, or T3 and BMP-2. Indirect immunocytochemistry revealed that in the presence of 1% FBS, approximately 30% of the cells differentiated into β-III-tubulin expressing neurons, whereas 5% became O4 expressing; the remainder of the cells did not express either antigen (FIG. 3A and FIG. 3E). Compared to controls in 1% FBS (n=3; 23 NE), BMP-2 had no significant effect on the number (p>0.15; Tukey HSD; n=4; 38 NE) of oligodendrocytes produced per clone (FIG. 3B). However, BMP-2 increased neurite length in comparison to 1% FBS (FIG. 3B vs. 3A). In contrast, T3 increased (5-fold) the differentiation of oligodendrocytes (p<0.001; Tukey HSD; n=4; 24 NE) (FIG. 3A vs. 3C; FIG. 3E). In the presence of both BMP-2 and T3, BMP-2 (n=4; 38 NE) suppressed T3-induced oligodendrocyte differentiation of PDGF-generated progeny (p<0.001, T3 vs. T3+BMP-2; Tukey HSD), and neuronal numbers were equivalent to those observed in differentiation with BMP-2 alone (p>0.99; Tukey HSD) (FIG. 3C vs. 3D; FIG. 3E). In all cases, numbers of differentiated cells (10-13 neurons and/or oligodendrocytes) remained constant at approximately ⅓ of the total clone size (30-35%). GFAP-immunoreactive cells, indicative of astrocytes, were not detected in any of these culture conditions.

Figure 4:
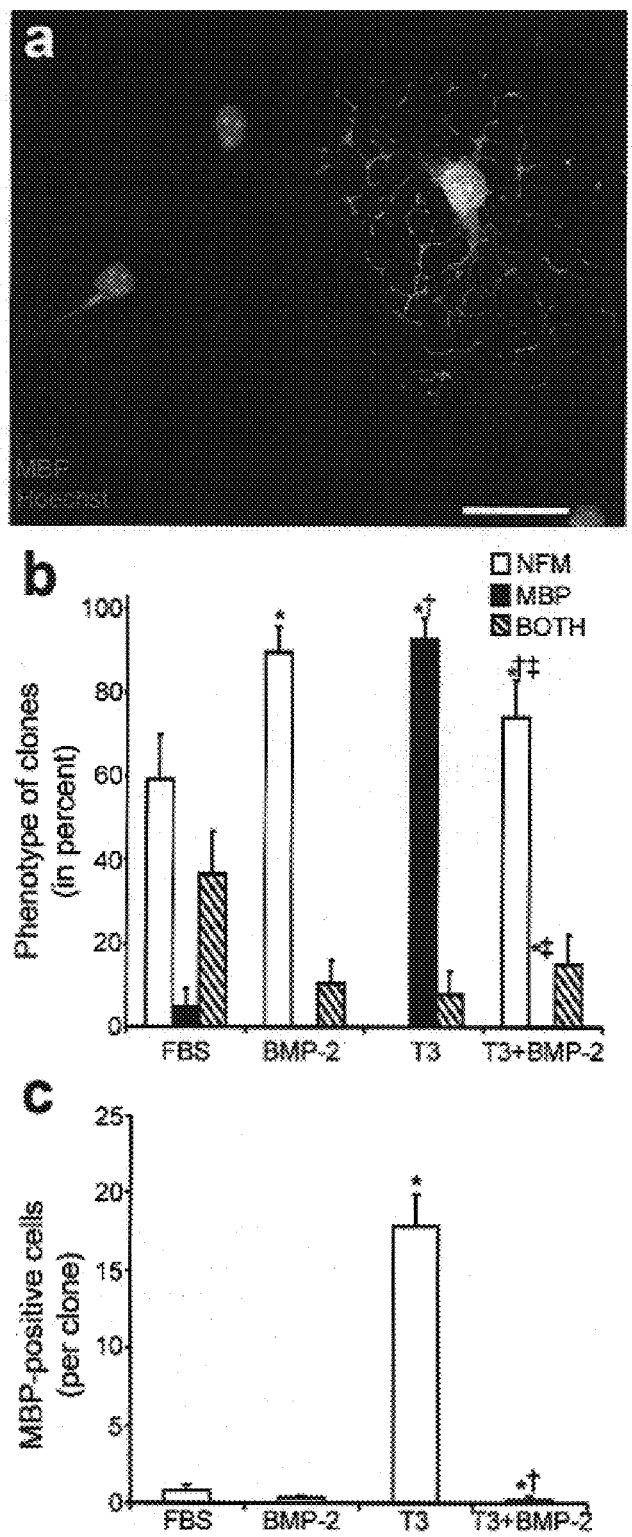
FIGS. 4A-4C show data indicating that T3 promotes and BMP-2 inhibits expression of mature oligodendroglial antigens in differentiating, primary PDGF-generated neurospheres. A, Photomicrograph of MBP- and NFM-immunoreactivity and Hoechst nuclear staining in PDGF-generated neurospheres differentiated in 1% FBS. B, BMP-2 increased percentage of clones expressing NFM compared to 1% FBS. T3 promoted oligodendrocyte maturation. Cells immunoreactive for both NFM and MBP were not observed. C, T3 increased MBP-expressing cell numbers compared to 1% FBS and BMP-2, which was suppressed by BMP-2. Scale bar=12.5 μm.

Cells with an oligodendroglial morphology that expressed O4 and an inner ring of β-III-tubulin were occasionally observed (FIG. 3F), but only when differentiated in FBS. While these early neuronal and oligodendroglial antigens may not definitively identify bona fide neurons and oligodendrocytes, it is more likely that T3 and BMP-2 direct the fate choices of uncommitted PRPs. BMP-2 and T3 induction of expression of more mature neuronal and oligodendroglial antigens, respectively, in differentiating primary PDGF-generated neurospheres was determined. PDGF-generated neurospheres differentiated for 2 DIV expressed neurofilament M (NFM; neurons) or myelin basic protein (MBP; oligodendrocytes), but both antigens were never observed in the same cell, regardless of the differentiation conditions (FIG. 4A). BMP-2 (n=3; 29 NE) increased the percentage of clones expressing NFM compared to differentiation in 1% FBS (p<0.05; Tukey HSD; n=3; 22 NE), while T3 (n=3; 26 NE) increased the number of MBP-only clones compared to 1% FBS, BMP-2 or T3 and BMP-2 (p<0.001; Tukey HSD; n=3; 27 NE) (FIG. 4B). In contrast, BMP-2, when present with T3, completely inhibited the generation of MBP-only clones (p<0.001 T3 vs. T3+BMP-2; Tukey HSD) (FIG. 4B). T3 (n=4; 29 NE) alone significantly increased the number of MBP-expressing cells produced per clone compared to 1% FBS (n=4; 25 NE), BMP-2 (n=4; 27 NE), and T3 and BMP-2 (p<0.001 T3 vs. 1% FBS, BMP-2, and T3 and BMP-2; Tukey HSD; n=4; 28 NE) (FIG. 4C). These data indicate that BMP-2 suppresses oligodendroglial differentiation but promotes neuronal maturation, whereas T3 promotes the formation of oligodendrocytes from PDGF-generated neurospheres.

Ventral forebrain PRPs therefore can generate neurons, and these neurons arise from a common neuron-oligodendrocyte precursor that can be induced to undergo neuronal differentiation with BMP-2, and oligodendroglial differentiation with thyroid hormone, triiodothyronine (T3). A common neuron/oligodendrocyte precursor may exist in the developing forebrain. First, in vivo, a subset of PDGFRα-expressing cells co-express the TOAD-64 neuronal antigen. Second, PRPs give rise to parvalbumin-immunoreactive, GABAergic interneurons. Third, tangential migration of both oligodendrocytes and neurons is disrupted in Dlx1/2 mutant mice, and BMP-2 enhances the generation of pure GABAergic neuronal clones at the expense of mixed neuronal/oligodendroglial clones from premigratory stage MGE or LGE progenitors (Yung et al., *Proc Natl Acad Sci USA* 99:16273 (2002)). Lastly, in vivo (Price et al., *Development* 104:473 (1988); Grove et al., *Development* 117:553 (1993)) and in vitro (Williams et al., *Neuron* 7:685 (1991)) retroviral lineage tracing studies of the E16 cortex have demonstrated the existence of clones that could generate both neurons and white matter cells or neurons and oligodendrocytes, respectively, which have been suggested as the cerebral equivalent of the O-2A progenitor. It is likely that the cells labelled were in fact PRPs that had migrated from the MGE to the cortex by E16, preliminary findings that PRPs are present in the E16 cortex. Taken together, the data suggest a common precursor generates oligodendrocytes and a subset of the interneurons in the forebrain, and these results indicate that it is PRP.

Example 5

This example includes data indicating that BMP-2 with CNTF suppresses the expression of OLIG2 and promotes astroglial differentiation. The astroglial population is distinct from that of differentiated neurons and oligodendrocytes.

GFAP-immunoreactive astrocytes were absent in PDGF-generated neurospheres differentiated in BMP-2. Other investigators have reported that BMPs induce astrocyte differentiation of O-2A progenitors in vitro (Mabie et al., *J Neurosci* 17:4112 (1997)) and glial progenitors in vivo (Gomes et al., *Dev Biol* 255:164 (2003)).

Figure 5:
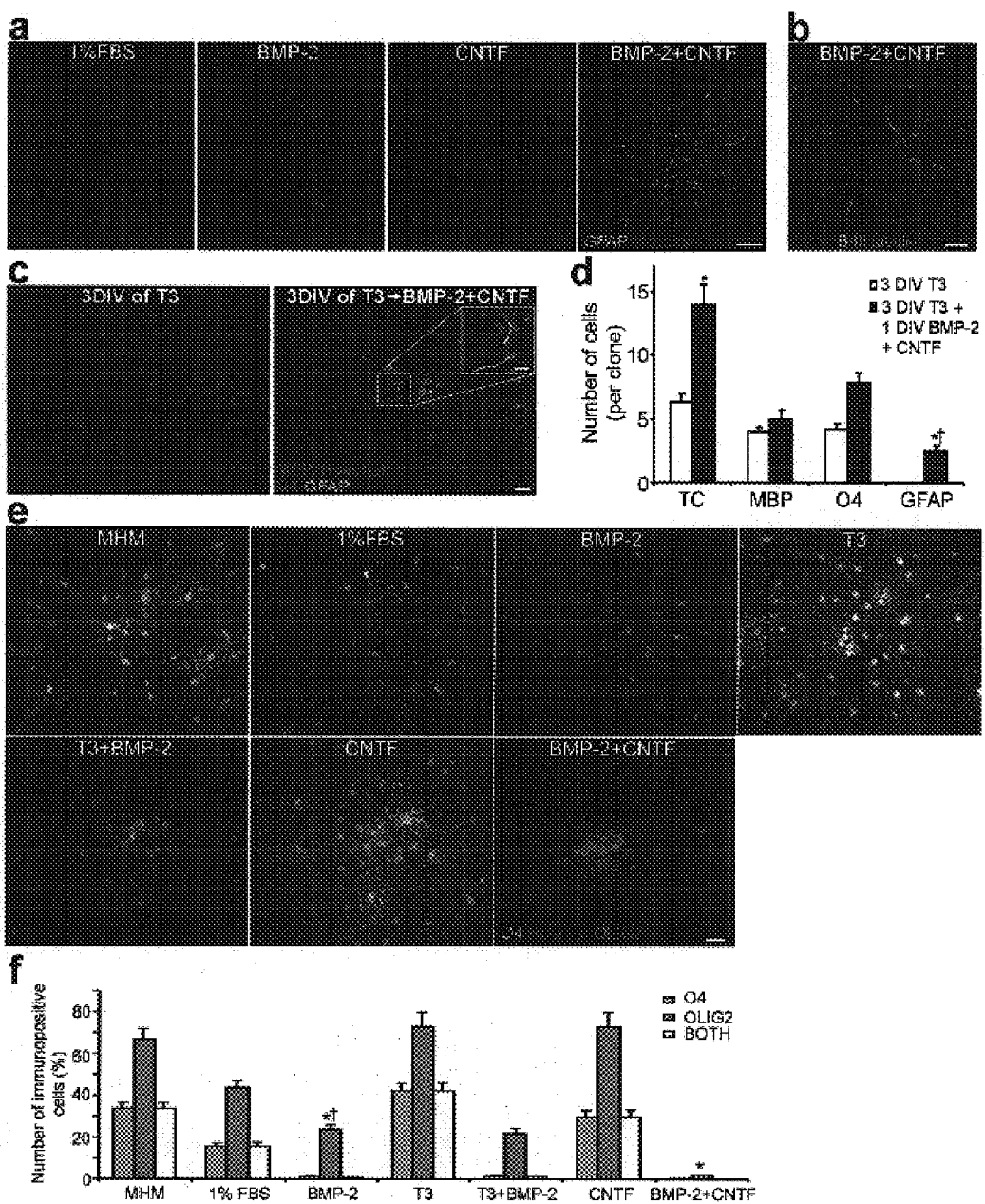
FIGS. 5A-5F show data indicating that BMP-2 and CNTF promote astroglial differentiation of an apparently distinct cell population. A, Astroglial differentiation of PDGF-generated neurospheres is evident after 2 days treatment with BMP-2 and CNTF. B, neuronal differentiation of PDGF-generated neurospheres is not suppressed by BMP-2 and CNTF treatment. C, differentiation in T3 promoted oligodendroglial and not astroglial differentiation in primary PDGF-generated neurospheres, and D, addition of BMP-2 and CNTF after the second day resulted in greater cell survival and a significant number of cells adopted an astroglial cell fate, but not at the expense of oligodendrocytes. E, F, BMP-2 suppresses O4 expression as efficaciously as BMP-2 and CNTF together, but BMP-2 and CNTF together are more effective at suppressing OLIG2 expression than BMP-2 alone. Scale bars in A, B, C, inset in C, and E are 50, 50, 50, 25, and 25 μm, respectively. TC=total cell number.

Additional studies were undertaken to ascertain the potential of PDGF-generated progeny to differentiate into astrocytes in the presence of CNTF, another factor known to induce astrocyte differentiation of O-2A progenitors (Hughes et al., *Nature* 335:70 (1988)). CNTF on its own did not induce GFAP expression in PDGF-generated progeny (FIG. 5A). It has been previously shown that LIF and BMP signaling can synergize to induce astrocyte differentiation of fetal neural progenitors (Nakashima et al., *Science* 284:479 (1999)). Studies on synergistic signaling may also reveal astrocyte differentiation in PDGF-generated neurospheres. When PDGF-generated progeny were differentiated in the presence of BMP-2 and CNTF, a large number of GFAP-immunoreactive cells with astrocyte morphology were apparent (FIG. 5A). Indeed, PDGF-generated neurospheres differentiated into neurons and astrocytes, but not oligodendrocytes, with BMP-2 and CNTF (FIG. 5B). In addition, numbers of neurons that differentiated in the presence of BMP-2 and CNTF (8±1; 24 NE) were not significantly different from the numbers observed with either BMP-2 alone or BMP-2 and T3. In contrast, the numbers of undifferentiated cells were dramatically reduced from 65-70% in FBS, BMP-2, T3 and BMP-2 and T3 conditions to 2-4% (24 NE) in the presence of BMP-2 and CNTF. Thus, PRP progeny have the potential to differentiate into astrocytes.

The findings that the PRP progeny differentiate into astrocytes in the presence of BMP-2 and CNTF suggest there may be a population of cells distinct from the N/O cells. If this were the case, then PDGF-generated neurospheres treated with T3, followed by BMP-2 and CNTF should yield clones that contain both oligodendrocytes and astrocytes.

Neurospheres (6 DIV) were differentiated in the presence of T3 for 3 DIV or in the presence of T3 with BMP-2 and CNTF added after the second day. Addition of BMP-2 and CNTF was delayed by two days to ensure the oligodendrocytes had been specified by the N/O cells and to prevent their predominant differentiation into neurons by BMP-2. Neurospheres that had BMP-2 and CNTF added to them after 2 DIV in T3 contained both MBP-immunoreactive oligodendrocytes (4.9±0.7; n=3, 34 NE) and GFAP-immunoreactive astrocytes (2.4±0.4). In contrast, cultures differentiated in T3 contained oligodendrocytes (3.9±0.4), but no astrocytes (FIG. 5C, D). Furthermore, the number of oligodendrocytes were not reduced when BMP-2 and CNTF were added, indicating that BMP-2 and CNTF do not promote differentiation of astrocytes from cells capable of oligodendrocyte differentiation.

It has been previously reported that BMP-2 overexpression in the chick spinal cord decreased expression of OLIG2 and oligodendrocyte specification (Mekki-Dauriac et al., *Development* 129:5117 (2002)). More recently, OLIG2 has also been found to directly suppress the astrocyte differentiation pathway (Fukuda et al., *Cell Death Differ* 11:196 (2004)).

To determine if OLIG2 expression is suppressed by BMP-2 or by BMP-2 and CNTF in PDGF-generated progeny, OLIG2 and O4 expression was studied by indirect immunocytochemistry after 6 DIV PDGF-generated neurospheres had been differentiated for 2 DIV (FIG. 5E, F). BMP-2 significantly reduced expression of OLIG2 in PDGF-generated progeny compared to MHM, 1% FBS, T3, T3+BMP-2, and CNTF. However, OLIG2 expression was still observed in cultures differentiated in BMP-2, albeit in fewer cells and at a relatively reduced level. Although CNTF had no effect on OLIG2 or O4 expression on its own, when combined with BMP-2, PDGF neurospheres lost virtually all OLIG2 and O4 expression (FIG. 5E, F). Loss of OLIG2 expression alone cannot account for the induction of astroglial differentiation by BMP-2 and CNTF, considering that in the other differentiation conditions astrocytes did not emerge even though a substantial number of cells did not express OLIG2. These data indicate that BMP-2 alone reduces OLIG2 expression, which may suppress oligodendrocyte differentiation and promote neuronal differentiation, whereas BMP-2 and CNTF together further reduce levels of OLIG2 expression in PDGF-generated progeny, and promote astrocyte differentiation in vitro.

Although not wishing to be bound to any theory, BMP-2 and CNTF may depend on a complex of the transcription factors Stat3, Smad1, and the co-activators p300/CBP, which have been shown to induce astrocyte differentiation of fetal neural progenitors (Nakashima et al., *Science* 284:479 (1999)). A lack of such co-operative signaling may explain previous observations that BMP signaling failed to promote astroglial differentiation (Wada et al., *Dev Biol* 227:42 (2000); Mekki-Dauriac et al., *Development* 129:5117 (2002)), although this may also be due to heterogeneity of OLP populations. The finding that BMP and CNTF signaling co-operates in the differentiation of astrocytes correlates with the repression of OLIG2 (and perhaps OLIG1) expression expand previous observations that OLIG1/2 suppress astrocyte cell fate specification (Zhou et al., *Cell* 109:61 (2002)) and glial fibrillary acidic protein (GFAP) expression (Gabay et al., *Neuron* 40:485 (2003); Fukuda et al., *Cell Death Differ* 11:196 (2004)). Even if PRPs do not generate astrocytes during embryonic development, their contribution to glial scarring in injury has not been assessed, which leaves the possibility that PRPs may generate astrocytes in vivo.

Example 6

This example includes data indicating that neurosphere generation by PDGF depends at least in part upon SHH signaling.

Signaling by SHH is necessary for the generation of OLPs in the mammalian forebrain (Nery et al., *Development* 128:527 (2001); Tekki-Kessaris et al., *Development* 128:2545 (2001)). To determine whether proliferation of PRPs may be sensitive to SHH signaling, dissociated MGEs (10,000 cells/ml) were grown in 100 ng/ml of PDGF-AA alone, or together with 5 µM cyclopamine, an inhibitor of SHH signaling (Cooper et al., *Science* 280:1603 (1998); Taipale et al., *Nature* 406:1005 (2000)). Neurospheres generated in the presence of cyclopamine were smaller than those generated in PDGF-AA+DMSO controls (compare FIG. 6A to 6B). Cyclopamine also reduced the number of PDGF-AA-generated neurospheres by 5-fold (p<0.003; t test; n=3) (FIG. 6C). There were large numbers of phase-bright differentiating cells in both conditions (indicated by arrows in FIG. 6B), indicating that the decrease in neurosphere numbers and size is likely not a result of a non-specific toxic effect.

Since inhibition of SHH signaling attenuated the proliferation of PRPs, the effect of increasing SHH signaling on the number of neurospheres generated in the presence of PDGF was studies. Primary cells from dissociated MGEs were cultured in the presence of PDGF-AA, 2 µg/ml of the 19-kDa amino-terminal fragment of SHH, or in the presence of both factors. FIG. 6D shows that, although SHH (n=3) had no effect on its own, significantly more neurospheres (p<0.05; LSD test) were generated in the presence of SHH and PDGF-AA (92±14; n=8) compared to PDGF-AA (60±9; n=8). Together, these data demonstrate that SHH is required in concert with PDGF signaling for the proliferation and/or survival of PRPs.

Example 7

This example includes data indicating that self-renewal of PRPs is dependent at least in part upon growth factor-dependent SHH signaling.

Initial studies suggested that PRPs lacked significant self-renewal capacity (FIG. 2F). However, these studies employed a defined culture media in which some factors required for self-renewal may be missing. To further study PRP self-renewal, primary PDGF neurospheres from the E14 MGEs of TgN(GFPU)5Nagy mice were grown for 7 DIV, individual neurospheres dissociated and transferred from single neurospheres onto poly-L-ornithine coated coverslips that had been plated with or without 200,000 primary 7 DIV EGF-generated progeny 2 days earlier.

Figure 7:
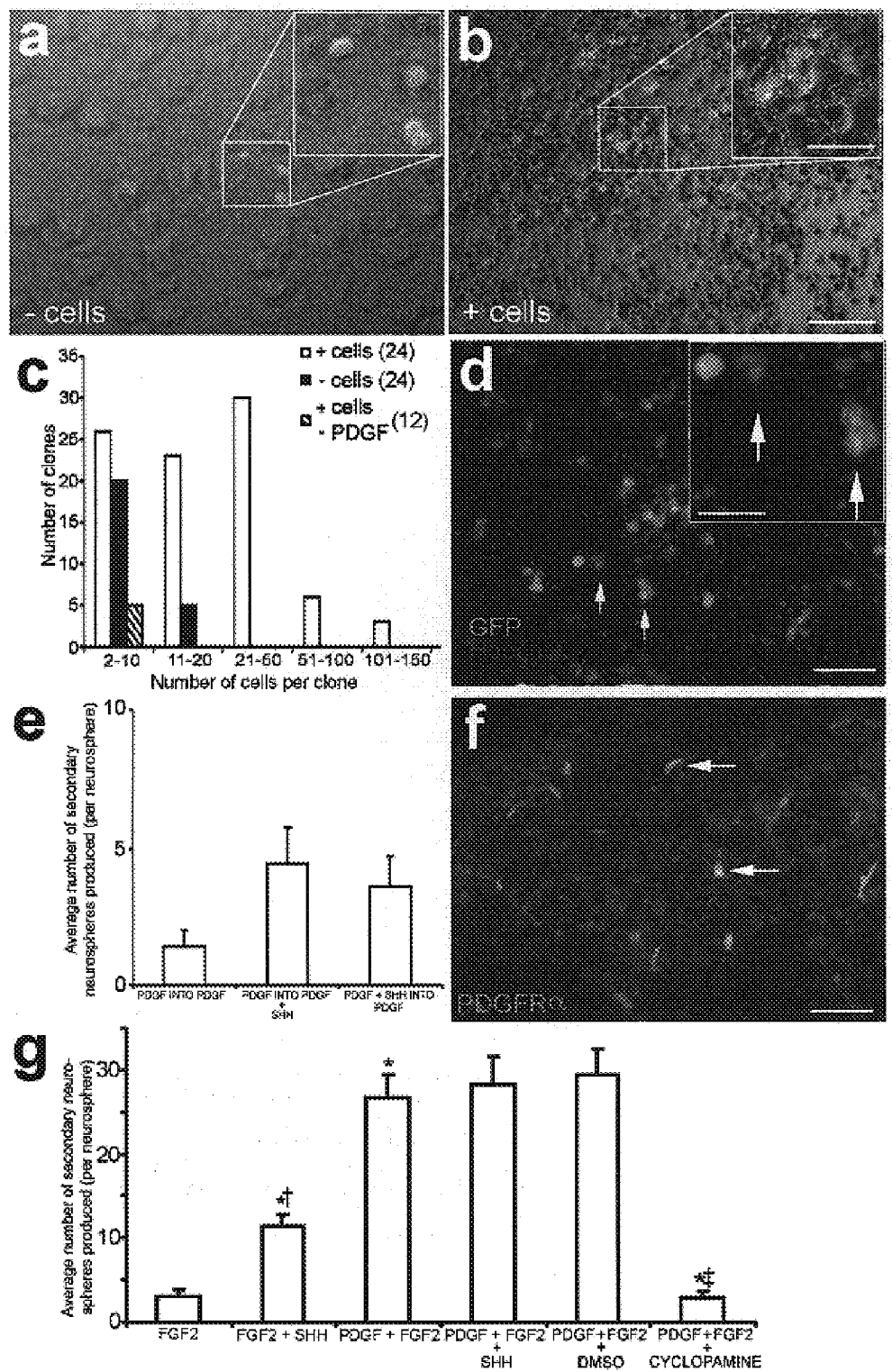
FIGS. 7A-7G show data indicating that PDGF and FGF2 signaling promote self-renewal of PRPs through an SHH-dependent pathway. GFP-expressing PDGF-generated neurospheres in PDGF A, without, or B, with EGF-feeder layer. C, numbers in parenthesis indicate number of neurospheres examined. D, Photomicrograph of GFP-expressing cells within a clone that express PDGFRα (indicated by arrows). E, no significant increase in generation of secondary neurospheres when primary PRPs were grown in conjunction with SH or when passaged into PDGF and SHH, compared to neurospheres generated and passaged in PDGF alone. F, PDGFRα-expressing cells co-express FGFR2 in the E14 MGE. G, FGF2 by itself had no significant effect on generation of secondary neurospheres by PDGF-generated neurospheres, except when combined with PDGF. SHH promoted generation of secondary neurospheres in FGF2, but not as robustly as PDGF and FGF2. Scale bars in B, inset in B, D, inset in D, and F are 100, 50, 50, 25, and 50 µm, respectively.

In the absence of the EGF-generated feeder layer or PDGF, large adherent colonies of GFP-positive cells were rarely observed (FIG. 7A). Most clones consisted of fewer than 10 cells (FIG. 7C). In contrast, single dissociates plated in the presence of PDGF and the EGF feeder layer produced many clones of GFP-labeled cells that contained greater than 10 cells (FIG. 7B, C), and many cells expressed PDGFRα (FIG. 7D). When single dissociates were plated on the EGF feeder layer but in the absence of PDGF, few clones were observed and all were less than 10 cells in number (FIG. 7C). These results suggest that some signals initiated by the EGF-generated feeder layer, whether soluble or contact-dependent, contribute to self-renewal of PRPs together with PDGF.

Since SHH enhanced the number of primary neurospheres generated by PDGF (FIG. 4), the effect of SHH could on formation of secondary neurospheres from primary PDGF-generated neurospheres was studied. No significant difference (p>0.99; Tukey HSD) in the number of secondary neurospheres generated when primary neurospheres were grown in the presence of PDGF and passaged into PDGF+SHH (n=3; 27 NE), or grown in the presence of PDGF and SHH (n=4; 37 NE) and passaged into PDGF, compared to those grown and passaged in PDGF (n=7; 69 NE) (FIG. 7E). The results indicate that self-renewal, as measured by the number of secondary neurospheres, cannot be augmented by SHH alone.

Signaling by FGF2, in combination with PDGF, has previously been shown to promote the self-renewal and inhibit the differentiation of O-2A progenitors in vitro, which normally lose responsiveness to PDGF after several rounds of cell division and differentiate (Bogler et al., *Proc Natl Acad Sci USA* 87:6368 (1990)). A recent study reports that full SHH actions on oligodendrocyte development depends upon FGF2-stimulated mitogen-activated protein kinase (MAPK) activity (Kessaris et al., *Development* 131:1289 (2004)).

Precursors that expressed PDGFRα in the ventral forebrain were studies for expression of FGF receptors. FGF2 can bind to the four know FGF receptors, FGFRs 1-4 (Reuss et al., *Cell Tissue Res* 313:139 (2003)). FGFR2 immunoreactivity was localized to nuclei in the ventricular zone and to scattered cells within the MGE (FIG. 7F). Some of the FGFR2-labelled nuclei outside the ventricular zone clearly belonged to cells that expressed PDGFRα (arrows in FIG. 7F), indicating that both signaling pathways may regulate the proliferation and self-renewal of PRPs.

To determine if FGF2 signaling alone, or together with SHH, augmented the generation of secondary neurospheres by PRPs, individual 6 DIV PDGF-generated neurospheres were dissociated and passaged in media containing either FGF2 (n=7; 64 NE) or FGF2 and SHH (n=7; 60 NE). No increase in self-renewal was evident in PDGF-generated progeny that had been passaged into FGF2 compared to PDGF (p>0.99; compare FIG. 7E to 7G). However, in the presence of FGF2, SHH significantly enhanced self-renewal of PRPs (FIG. 7G), in comparison to primary PDGF-generated neurospheres passaged into either FGF2 (p<0.05; Tukey HSD) or to PDGF (p>0.01; Tukey HSD; FIG. 7E).

The effect of PDGF and FGF2 in augmenting secondary neurosphere formation was studied. In the presence of PDGF+FGF2 (n=9; 78 NE), 27±3 secondary neurospheres were generated (FIG. 7G), indicating that both PDGF and FGF2 signaling contribute to self-renewal of PRPs, and this was not further increased when SHH was added (28±3 secondary neurospheres; p>0.99; Tukey HSD; n=5; 45 NE). The possibility that FGF2 is merely supporting proliferation of PRPs is unlikely, given that primary PDGF neurosphere formation was unaffected by 1 µM SU5402 (an FGFR tyrosine kinase inhibitor) (Mohammadi et al., *Science* 276:955 (1997)), which was able to block 90% of FGF2-induced NSC proliferation.

Despite the inability of added SHH to augment secondary PDGF neurosphere formation, co-operative actions of PDGF and FGF2 might be sufficient to support intrinsic SHH signaling, the latter of which is normally necessary for oligodendrocyte generation. Indeed, self-renewal of PRPs passaged into PDGF and FGF2 was dependent on SHH signaling, as cyclopamine reduced the generation of secondary neurospheres (3±1; n=4; 36 NE; FIG. 7G) to numbers closer to those obtained with PDGF (1±1) or FGF2 (3±1). Taken together, these findings indicate the full expression of self-renewal capacity by PRPs is dependent, at least in part, on activation of SHH signaling by both PDGF and FGF2.

PRPs have an extensive potential for expansion/self-renewal. Both PDGF and FGF2 were required for the formation of secondary neurospheres. In addition, PDGF and FGF signaling act through SHH to promote PRP self-renewal. Recent reports demonstrate that generation of OLPs by SHH is dependent on a basal level of MAPK activity, provided by FGF signaling (Kessaris et al., *Development* 131:1289 (2004)). It is possible that MAPK plays a role in the regulation of SHH signaling in PRP self-renewal. It is noteworthy that the maximal number of secondary PRPs (26-28 neurospheres), derived from a primary PRP, is approximately equivalent to the number of undifferentiated cells within each PRP clone. Furthermore, undifferentiated cells are largely eliminated when PRP clones are differentiated into neurons and astrocytes in the presence of BMP-2+CNTF, although the neuron numbers are unchanged.

Figure 8:
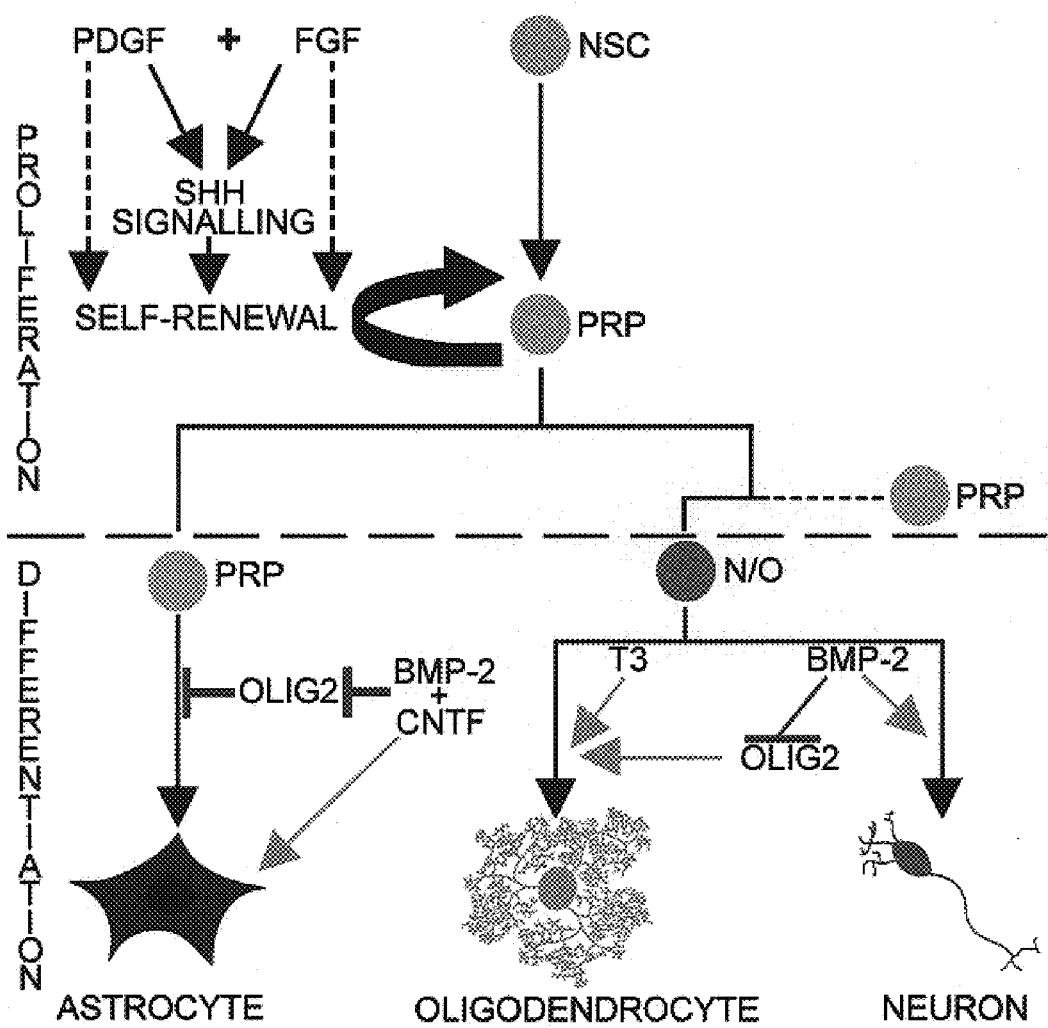
FIG. 8 is a schematic representation of self-renewal and differentiation of E14 ventral forebrain PRPs. NSCs generate PRPs in both PDGF and FGF to activate the SHH pathway for continued expansion. After expansion, levels of OLIG expression as well as the environment determine the fate of PRPs. High levels of OLIG expression, maintained by T3, support oligodendroglial differentiation, whereas decreasing levels of OLIG2 expression in the presence of BMP or BMP and CNTF promote generation of neurons and astrocytes, respectively.

Taken together with the largely mutually exclusive differentiation of neurons and oligodendrocytes in PRP clones, this leads to a proposed model for the lineage of PRPs (FIG. 8). As illustrated, PRPs are likely descendents of multipotent NSCs, which is supported by findings that they can be generated by primary EGF-responsive NSCs and have identical properties to the PRPs from the ventral forebrain.

Example 8

This example includes data indicating that PRPs are responsive to neurotrophin-3 (NT-3).

The effect of brain-derived neurotrophic factor (BDNF), neurotrophin-3 (NT-3), and nerve growth factor (NGF) on PRPs was determined. Cells were cultured as previously reported (Chojnacki et al., *J Neurosci* 24(48):10888 2004) in the presence of various combinations of PDGF, brain-derived neurotrophic factor (BDNF), NT-3, nerve growth factor (NGF), and the effects on neurosphere generation characterized. MHM is the defined medium used in cultures without growth factor.

Figure 9:
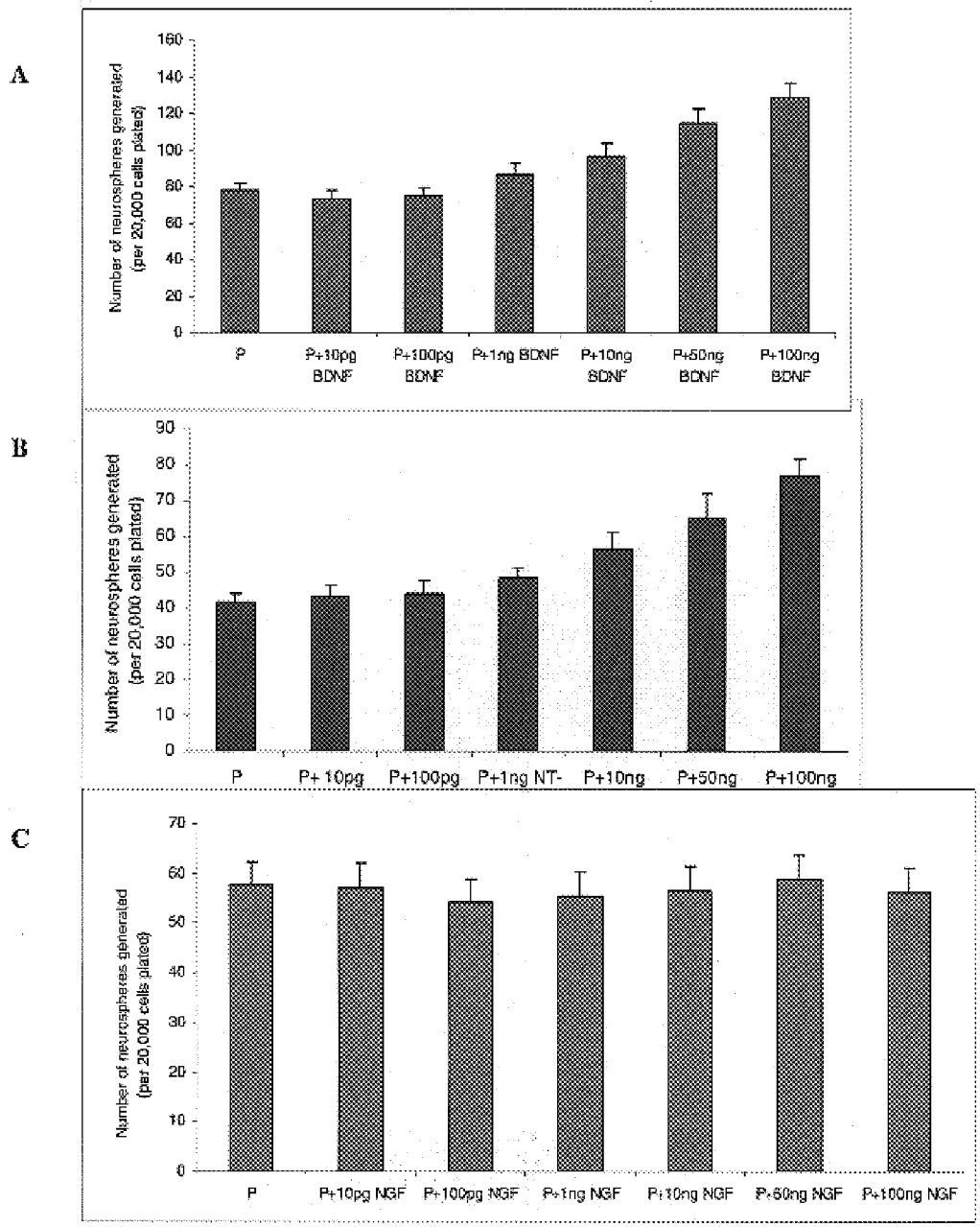
FIGS. 9A-9C show that neurospheres are produced when PRPs are generated in the presence of PDGF and BDNF or NT-3, but not NGF.
Figure 10:
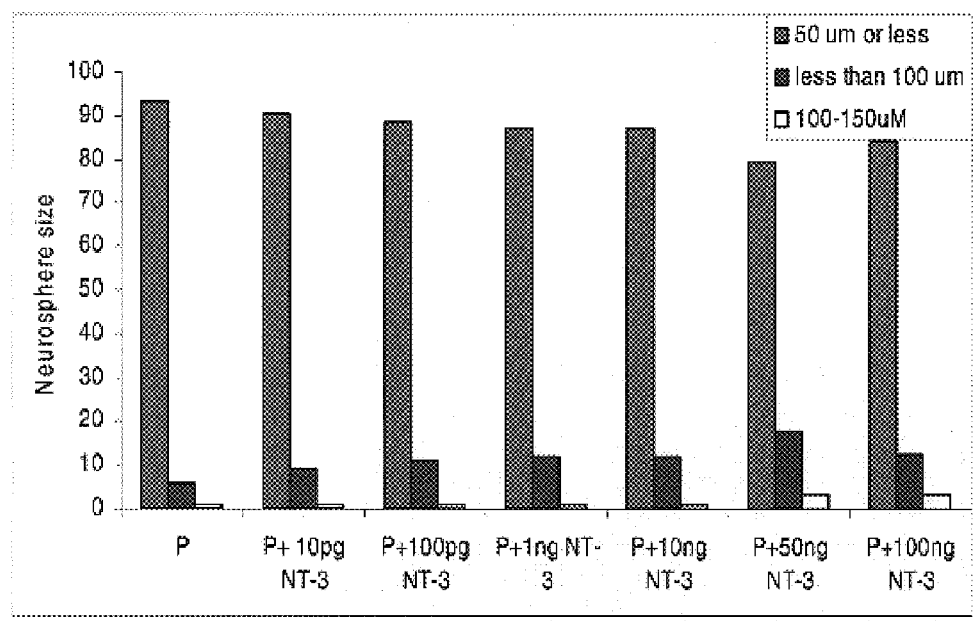
FIG. 10 shows that NT-3 and BDNF promote generation of larger neurospheres in the presence of PDGF.
Figure 11:
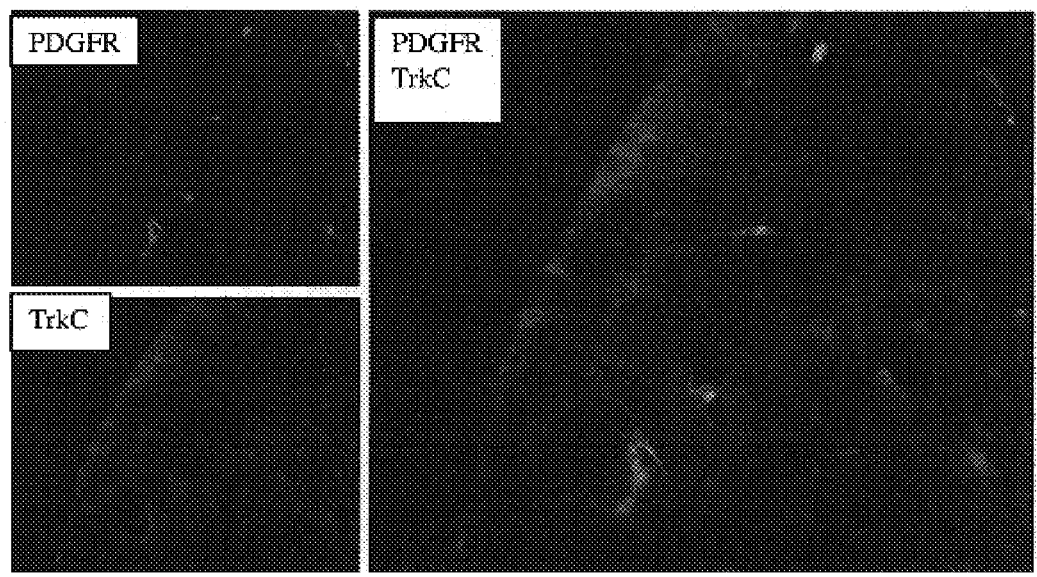
FIG. 11 shows that PRPs co-express PDGFRα and TrkC in the E14 ventral forebrain.
Figure 12:
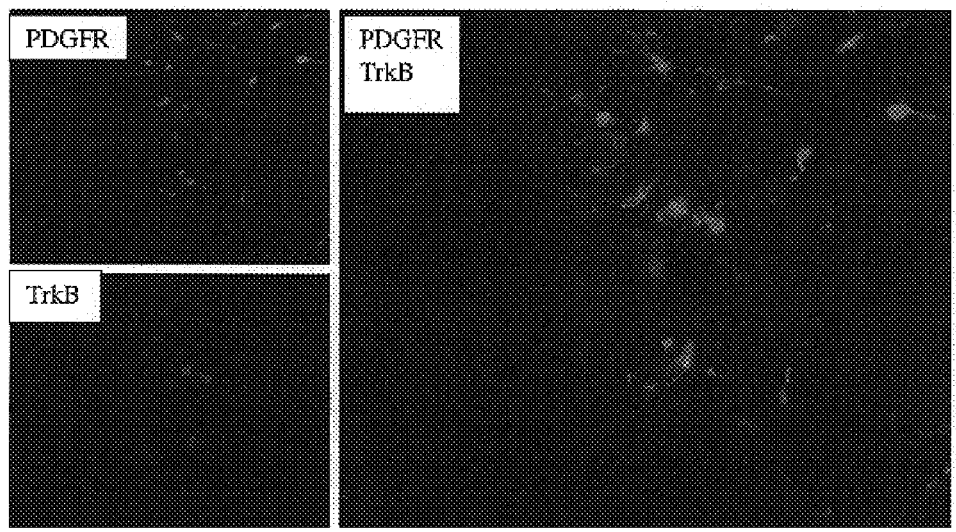
FIG. 12 shows that PRPs do not co-express PDGFRα and TrkB in the E14 ventral forebrain.
Figure 13:
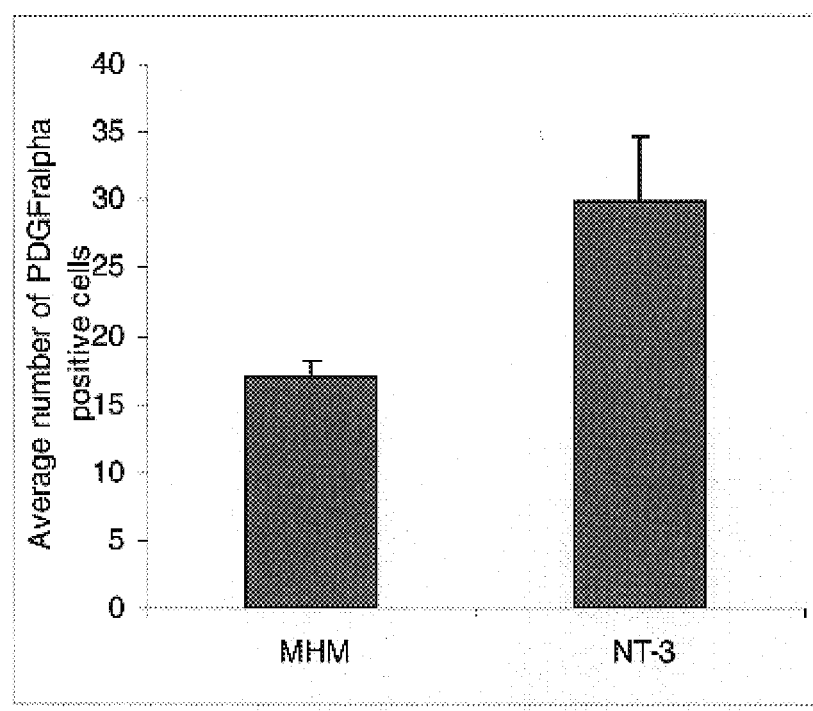
FIG. 13 shows that NT-3 apparently does not maintain the PRP population by promoting cell survival.
Figure 14:
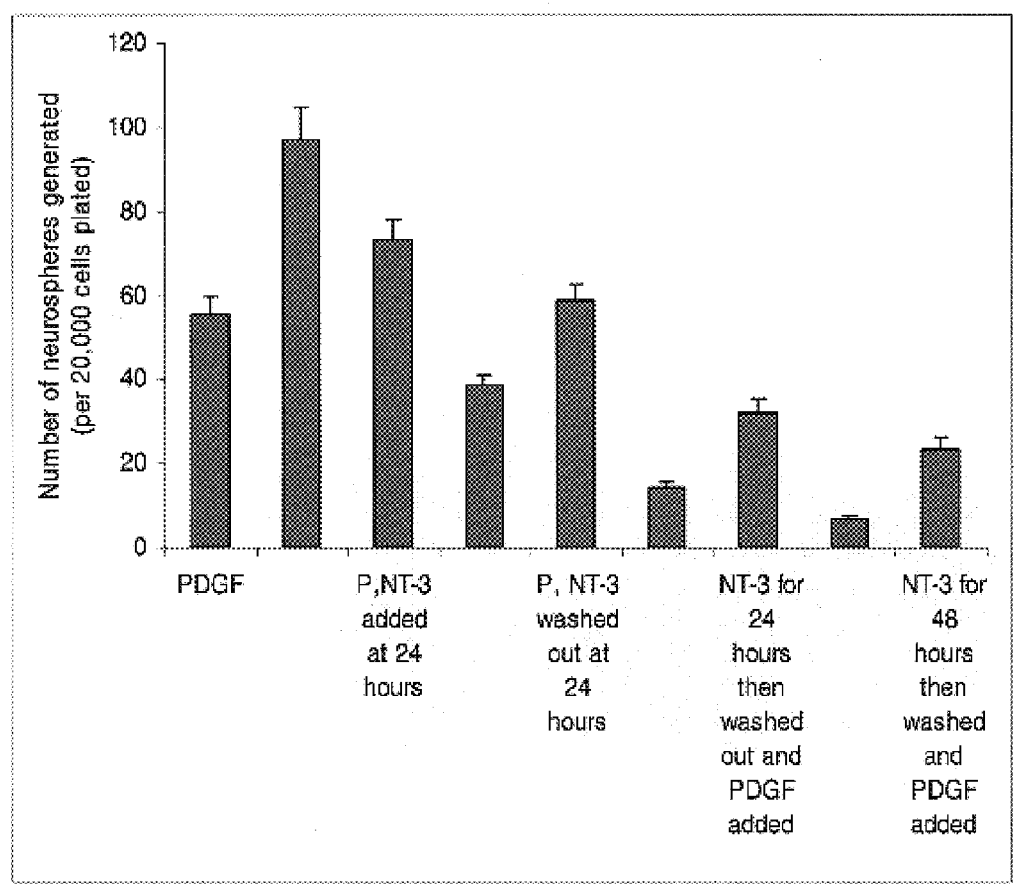
FIG. 14 shows that an initial 24 hour treatment with NT-3 was more effective at promoting generation of neurospheres than continued exposure to NT-3 after the first 24 hours.

As illustrated in FIG. 9, more neurospheres are produced when PRPs are generated in the presence of PDGF and BDNF or NT-3, but not NGF. FIG. 10 shows that NT-3 and BDNF promote the generation of larger neurospheres in the presence of PDGF. FIG. 11 shows that PRPs co-express PDGFRα and TrkC in the E14 ventral forebrain. FIG. 12 shows that PRPs do not co-express PDGFRα and TrkB in the E14 ventral forebrain Dissociated primary cells were cultured in 24-well plates with or without NT-3 for 24 hours, stained for PDGFRα and Tunel, and the number of labeled cells counted. As illustrated in FIG. 13, more PDGFRα-labeled cells were found in the NT-3 treated culture after 24 hours, but no Tunel and PDGFRα co-labeled cells were observed in either condition. The results suggest that NT-3 does not maintain the PRP population by promoting cell survival. As illustrated in FIG. 14, an initial 24 hour treatment with NT-3 was more effective at promoting the generation of neurospheres than continued exposure to NT-3 after the first 24 hours. The data again suggests that NT-3 does not promote the survival of PRPs.

Figure 15:
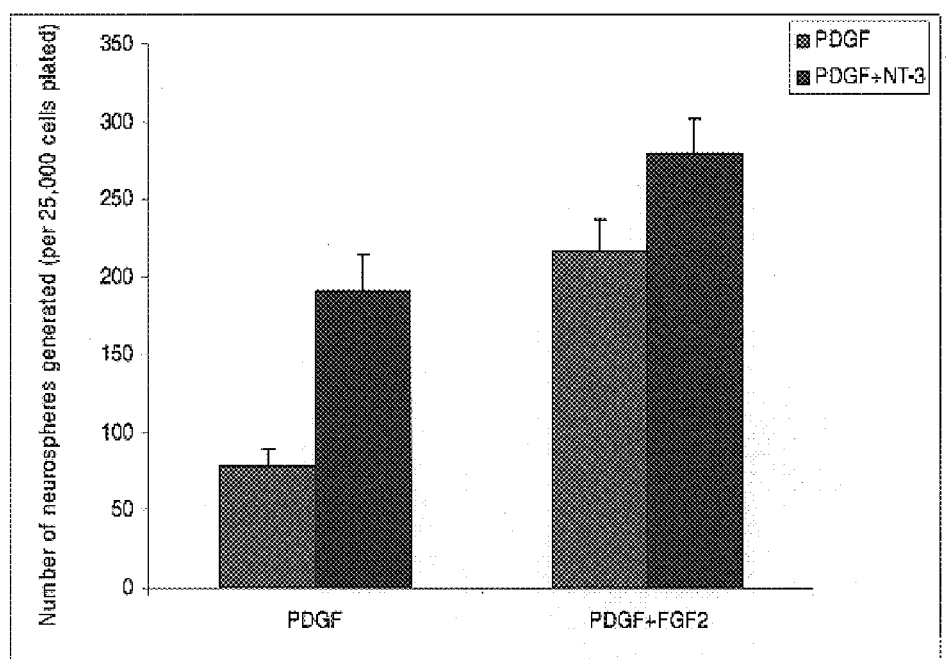
FIG. 15 shows that neurospheres initially generated in PDGF and NT-3 produced more secondary neurospheres in either condition.

Seven day old primary neurospheres generated in either PDGF or PDGF+NT-3 were dissociated and plated (25,000 cells/mL) in either PDGF or PDGF and FGF2. As illustrated in FIG. 15, neurospheres initially generated in PDGF and NT-3 produced more secondary neurospheres in either condition. The data indicates that NT-3 promotes self-renewal of PRPs.

PRPs are a unique population of oligodendrocyte precursors, with both distinct and similar properties to other OLPs described previously (Liu et al., *Trends Neurosci* 26:410 (2003); Noble et al., *Dev Biol* 265:33 (2004); Rowitch, *Nat Rev Neurosci* 5:409 (2004)). The in vitro studies have revealed that these precursors are heterogeneous in their ability to generate neurons and subtypes of astrocytes and this is dependent on the CNS region and developmental period of isolation. The early development of hindbrain OLPs is unimpaired in OLIG2 null mice (Lu et al., *Cell* 109:75 (2002)), whereas there is a complete absence of OLPs in the spinal cord, suggesting that OLPs in vivo are also a heterogeneous population. Even within the forebrain, we found that there may be heterogeneity in PRPs based on the expression of TOAD-64. Therefore, if forebrain PRPs generate neurons in vivo, it may only be a subpopulation of PRPs that posses this capability. PRPs may maintain the capacity to generate neurons through to adulthood. If human PRPs can be generated as neurospheres, this would permit isolating and expanding neural precursors for transplantation in white matter for the treatment of injury or disease.

What is claimed is:

1. A method of producing mammalian PDGF-responsive neural precursor (PRP) cells that express PDGF receptor alpha, comprising:
    (a) culturing brain tissue from a mammalian embryo in a culture medium containing PDGF and allowing proliferation of the PRP cells to produce primary neurospheres of the PRP cells, wherein the culture medium does not contain EGF; and
    (b) passaging the primary neurospheres of the PRP cells with PDGF and FGF-2 for self-renewal of the PRP cells.

2. The method of claim 1, wherein said mammalian embryo is human, non-human primate, mouse, rattus, bovine, porcine, equine, cavia, lagomorph, canine or feline.

3. The method of claim 1, wherein the culture medium of step (a) does not contain TGF.

4. The method of claim 1, wherein the culture medium of step (a) does not contain FGF.

5. The method of claim 1, wherein the brain tissue is obtained from ganglionic eminence.

6. The method of claim 1, wherein the brain tissue is obtained from medial ganglionic eminence.

7. A method of producing mammalian PDGF-responsive neural precursor (PRP) cells that express PDGF receptor alpha, comprising:
    (a) culturing brain tissue from a mammalian embryo in a culture medium containing PDGF and allowing proliferation of the PRP cells to produce primary neurospheres of the PRP cells, wherein the culture medium does not contain FGF; and
    (b) passaging the primary neurospheres of the PRP cells with PDGF and FGF-2 for self-renewal of the PRP cells.

8. The method of claim 7, wherein the brain tissue is obtained from medial ganglionic eminence.

9. The method of claim 7, wherein the brain tissue is obtained from ganglionic eminence.

10. The method of claim 7, wherein said mammalian embryo is human, non-human primate, mouse, rattus, bovine, porcine, equine, cavia, lagomorph, canine or feline.

11. The method of claim 7, wherein the culture medium of step (a) does not contain TGF.

12. A method of producing mammalian PDGF-responsive neural precursor (PRP) cells that express PDGF receptor alpha, comprising
    a) culturing medial ganglionic eminence from a mammalian embryo in a culture medium containing PDGF and allowing proliferation of the PRP cells to produce primary neurospheres, wherein the culture medium does not contain FGF, and
    b) passaging the primary neurospheres of the PRP cells with PDGF and FGF-2 for self-renewal of the proliferated PRP cells.

13. The method of claim 12, wherein the culture medium of step (a) does not contain TGF.

14. The method of claim 12, wherein said mammalian embryo is human, non-human primate, mouse, rattus, bovine, porcine, equine, cavia, lagomorph, canine or feline.

15. A method of producing mammalian PDGF-responsive neural precursor (PRP) cells that express PDGF receptor alpha, comprising
    a) culturing medial ganglionic eminence from a mammalian embryo in a culture medium containing PDGF and allowing proliferation of the PRP cells to produce primary neurospheres, wherein the culture medium does not contain EGF, and
    b) passaging the primary neurospheres of the PRP cells with PDGF and FGF-2 for self-renewal of the proliferated PRP cells.

16. The method of claim 15, wherein the culture medium of step (a) does not contain FGF.

17. The method of claim 15, wherein the culture medium of step (a) does not contain TGF.

18. The method of claim 15, wherein said mammalian embryo is human, non-human primate, mouse, rattus, bovine, porcine, equine, cavia, lagomorph, canine or feline.

* * * * *